(12) United States Patent
Pfaff et al.

(10) Patent No.: US 10,347,478 B2
(45) Date of Patent: Jul. 9, 2019

(54) SYSTEMS AND METHODS FOR EXTRACTING MASS TRACES

(71) Applicant: Thermo Fisher Scientific (Bremen) GmbH, Bremen (DE)

(72) Inventors: Hans Pfaff, Ganderkesee (DE); Christoph Henrich, Bremen (DE); Robert Malek, Lilienthal (DE); Katja Tham, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/988,858

(22) Filed: May 24, 2018

(65) Prior Publication Data

US 2018/0350577 A1 Dec. 6, 2018

(30) Foreign Application Priority Data

Jun. 2, 2017 (EP) .................................... 17174385
May 4, 2018 (EP) .................................... 18170779

(51) Int. Cl.
*H01J 49/00* (2006.01)
*G01N 30/86* (2006.01)
*G01N 30/72* (2006.01)

(52) U.S. Cl.
CPC ...... *H01J 49/0036* (2013.01); *G01N 30/8631* (2013.01); *H01J 49/0004* (2013.01); *G01N 30/72* (2013.01); *G01N 2030/8648* (2013.01)

(58) Field of Classification Search
USPC ................................................ 250/282, 281
See application file for complete search history.

(56) References Cited

U.S. PATENT DOCUMENTS

| 5,300,771 A * | 4/1994 | Labowsky ........... H01J 49/0027 250/282 |
| 2004/0108452 A1* | 6/2004 | Graber ............... G01N 33/6803 250/281 |
| 2005/0086017 A1* | 4/2005 | Wang ................. G06K 9/00496 702/85 |
| 2006/0284069 A1* | 12/2006 | Le Blanc ........... G01N 30/8641 250/282 |
| 2008/0234948 A1 | 9/2008 | Walk et al. |
| 2016/0071711 A1 | 3/2016 | Ikegami |

FOREIGN PATENT DOCUMENTS

WO    2006/130983 A1    12/2006

* cited by examiner

*Primary Examiner* — Kiet T Nguyen
(74) *Attorney, Agent, or Firm* — David A. Schell

(57) ABSTRACT

A method of extracting a mass trace from mass spectrometry data of a mass stream emitted from a separation device as a function of a separation parameter, the method comprising, receiving the mass spectrometry data, wherein the mass spectrometry data comprise a plurality of mass spectra each obtained for respective values of the separation parameter; identifying, from the plurality of mass spectra, a sequence of three or more intensity peaks that are ordered according to the separation parameter, wherein said identifying the sequence of intensity peaks comprises, selecting an initial intensity peak at an initial mass, and for each other intensity peak, selecting said intensity peak based on at least the mass of an adjacent intensity peak in the sequence of intensity peaks, the method further comprising, providing a mass trace, for a given emitted compound of the mass stream, from the identified sequence of intensity peaks.

17 Claims, 12 Drawing Sheets

SYSTEMS AND METHODS FOR EXTRACTING MASS TRACES

FIELD OF THE INVENTION

The present invention relates to the analysis of mass spectrometer data, in particular the extraction of mass traces, for example to form extracted ion chromatograms.

BACKGROUND OF THE INVENTION

The use of mass spectrometry (MS) techniques has become invaluable across many fields where detailed analysis of various chemical, and often biological, samples is required. Such mass spectrometry analysis is used to identify the chemical makeup of given samples.

Straightforward analysis in a mass spectrometer typically involves the generation of ions from a chemical sample. The mass-to-charge ratio (m/z) and abundance of these ions are then measured by the mass spectrometer to produce a mass spectrum. The peaks (or centroids) in intensity at particular m/z values in such a mass spectrum provides a signature that indicates the relative abundance and mass of respective ions. This signature allows the compound (or compounds) that make up the original chemical sample to be identified.

For samples that comprise a large number of different compounds, such as biological samples, MS techniques are often combined with separation techniques. Separation techniques typically involve partitioning (or separation) of a sample, for example by washing a sample that is bound to a stationary phase with a solvent, such that various components of the sample are emitted from the sample as a function of a given separation parameter (or parameters) such as retention time. Common separation techniques include chromatography techniques—such as liquid chromatography (LC) or gas chromatography (GC). With combined chromatography and mass spectrometry techniques (such as LC/MS), the chromatographic technique causes different compounds (or analytes) to elute from the sample at different times (known as retention time) or, more typically, over a period of retention time. The compounds eluted at a given retention time are analysed using a mass spectrometer to produce a mass spectrum for that retention time. Thus, a typical chromatography/mass spectrometry analysis produces many individual mass spectra over a given period of retention time. These mass spectra vary as a function of retention time, indicating the variation of compounds eluted from the sample over the same time.

Analysis of these mass spectra as a function of the elution parameter allows not only individual eluted compounds to be identified, but also the sample as a whole to be identified or characterized. The elution parameter is typically retention time in the examples discussed above but may also be ion mobility, pH, ion size and/or other physio-chemical properties. Often such physio-chemical properties are proportional to the retention time. Typically, this analysis is done by generating mass traces (such as extracted ion chromatograms) for m/z values of interest. The m/z values of interest are themselves often determined based on the mass spectra. For example the m/z value of any intensity peak (in a spectrum) whose intensity falls above a certain threshold may be considered an m/z value of interest. A given mass trace is formed of the intensities of peaks in the mass spectra at (or around) a given m/z value. These intensities are then plotted as a function of elution parameter. A mass trace having a maximum (and optionally fulfilling certain other criteria such as a minimum abundance and or conformance to an expected signal model) is considered an event (or feature) and such a feature can be used in identifying a particular eluted compound.

The number of individual mass spectra produced by such combined separation/mass spectrometry techniques is often very large (for a typical LC/MS analysis it can be of the order of thousands of mass spectra). This means, in turn the number of mass traces identified is often correspondingly large (e.g. of the order of around 1,000 to 1,000,000 mass traces). Given this, the generation of mass traces typically requires automation.

The existing method for generating mass traces uses a pre-defined m/z window that is measured during elution. This is a range of m/z values, typically, centred on the m/z value of interest and any intensity peak in the mass spectra falling within this m/z window forms part of the mass trace for that m/z value. The window width is usually specified by a user or software designer, and must be adjusted by hand in the event of any errors in the mass trace generation. Automated determination of parameters (such as chromatographic peak width and its time dependence) is known from U.S. Pat. No. 9,395,341, but still uncommon.

SUMMARY OF THE INVENTION

It is an object of the invention to provide an improved system for generating mass traces following separation mass spectrometry analysis. In particular it has been observed that if, during the elution of a first compound with an intensity peak (which may be represented as a centroid) at a given m/z value, a second compound with another intensity peak at a similar m/z value also elutes, the measured m/z values of one or both peaks may be distorted. In particular there is a tendency for the two peaks to be deflected towards each other in m/z space.

Such deflection can lead to errors in the mass traces generated by methods of the prior art, as outlined above. In particular, the deflection may be such that some m/z intensity peaks that would usually fall inside the m/z window for a given mass trace, are now deflected outside of the m/z window. This leads to points of the mass trace being absent, and in some cases events being missed, or misidentified. This is described in more detail below with reference to FIG. 1c.

In the present invention new methods and systems for generating mass traces are proposed. The invention provides a method for extracting a mass trace by identifying a first candidate centroid (or intensity peak) and following the mass trace along subsequent centroids, identifying further centroids of the mass trace based on the m/z value of the adjacent centroids already identified as part of the mass trace.

In a first aspect there is provided a computer implemented method of extracting a mass trace (such as an extracted ion chromatogram) from mass spectrometry data of a mass stream (or ion stream or other stream or flow of analytes) emitted from a separation device as a function of a separation parameter (or separation dimension). It will be appreciated that the separation device may be any device that can cause analytes to be separated from a sample provided to the separation device. For example the separation device may be any of: a liquid (or gas) chromatograph (or chromatography column); an imaging device, such as a matrix-assisted laser desorption ionization (MALDI), or secondary ion mass spectrometry (SIMS) imaging device, and so on.

In this aspect the mass spectrometry data are generated by analysis in a mass spectrometer and the method comprises receiving the mass spectrometry data, wherein the mass spectrometry data comprise a plurality of mass spectra each obtained for respective values of the separation parameter. Similarly the separation dimension may be anything which parameterizes said separation. In chromatography devices this is typically retention time, whereas in imaging devices this may be the position of a beam of probe on the surface of a sample.

The method continues with by identifying, from the plurality of mass spectra, a sequence of three or more intensity peaks that are ordered according to the separation parameter. Said identifying the sequence of three or more intensity peaks comprises selecting an initial intensity peak at an initial mass, and for each other intensity peak of the sequence of intensity peaks, selecting said intensity peak based on at least the mass of an adjacent intensity peak in the sequence of intensity peaks.

A mass trace, for a given emitted compound of the mass stream, is provided from the identified sequence of intensity peaks. Typically, the mass trace is formed from at least the identified intensity peaks.

The step of identifying a sequence of three or more intensity peaks may be carried out in the alternate by selecting an initial intensity peak at an initial mass and an initial value of the separation parameter to form part of a mass trace, and repeatedly selecting further intensity peaks at further values of the separation parameter to form part of the mass trace based on at least the mass of one or more previously selected intensity peaks at adjacent values of the separation parameter.

This aspect advantageously allows mass traces to be followed, and ultimately extracted, from the mass spectrometry data, with a greater reliability in the presence of m/z deflections in the mass spectrometry data such as those described above. This is because the method effectively follows the mass trace along its path and is thus able to track smooth deflections in the m/z direction.

Typically for each other intensity peak of the sequence of intensity peaks, said intensity peak is selected conditional on said intensity peak being at a respective mass that is within a respective range (or variance) about a respective expected mass, wherein the respective expected mass is determined based on at least the mass of an adjacent intensity peak in the sequence of intensity peaks.

Said determining of the respective expected mass can be based on (or include) an average of the previously selected intensity peaks of the sequence. Said average may, optionally, be a weighted average and/or a windowed average.

In some embodiments the respective range is determined as a function of the intensity of the adjacent intensity peak.

In an embodiment of the method in the step of identifying, from the plurality of mass spectra, a sequence of three or more intensity peaks that are ordered according to the separation parameter, this step comprises selecting an initial intensity peak at an initial mass, and for each other intensity peak of the sequence of intensity peaks, selecting said intensity peak based on the mass and the separation parameter of an adjacent intensity peak in the sequence of intensity peaks.

In particular for each other intensity peak of the sequence of intensity peaks, said intensity peak is selected based on the mass difference of the mass of said intensity peak and the mass of the adjacent intensity peak and the difference of the separation parameter of said intensity peak and the separation parameter of the adjacent intensity peak. Preferably the other intensity peaks of the sequence of intensity peaks are selected in that way, that with an increasing difference of the separation parameter of an selected intensity peak and the separation parameter of the adjacent intensity peak the the mass difference of the mass of said selected intensity peak and the mass of the adjacent intensity peak has to be smaller.

The maximum of the allowed mass difference of the mass of a selected intensity peak and the mass of the adjacent intensity peak, the allowed mass window, can be given by a function of the difference of the separation parameter of said selected intensity peak and the separation parameter of the adjacent intensity peak. This function is preferably decreasing with the difference of the separation parameter of said selected intensity peak and the separation parameter of the adjacent intensity peak and can be expressed for example as an equation of an circle or an ellipse when one of its axes is the mass difference of the mass of a selected intensity peak and the mass of the adjacent intensity peak and the other axis is the difference of the separation parameter of said selected intensity peak and the separation parameter of the adjacent intensity peak.

The step of identifying a sequence of three or more intensity peaks may be carried out in the alternate by selecting an initial intensity peak at an initial mass and an initial value of the separation parameter to form part of a mass trace, and repeatedly selecting further intensity peaks at further values of the separation parameter to form part of the mass trace based on the mass of at least one or more previously selected intensity peaks at adjacent values of the separation parameter and the separation parameter of the intensity peak in the sequence of intensity peaks adjacent to the selected further intensity peak.

In particular the mass of at least one or more previously selected intensity peaks may define a mass window. Then the mass of the further selected intensity peak has to be in the range of the mass window. The defined mass window is decreasing further on with an increasing difference of the separation parameter of the further selected intensity peak and the separation parameter of its adjacent intensity peak in the sequence of intensity peaks.

This aspect advantageously allows mass traces to be followed, and ultimately extracted, from the mass spectrometry data, with a further enhanced reliability in the presence of m/z deflections in the mass spectrometry data such as those described above taking further into account the difference of the separation parameter of adjacent intensity peaks in the sequence of intensity peaks.

In an embodiment where the separation device comprises a chromatograph, the separation parameter typically comprises retention time. However it will be appreciated that retention time may be used as a proxy measure for other physio-chemical properties such as any of: ion mobility; pH; ion size; collision cross section; polarizability; etc.

Additionally, or alternatively, the separation parameter may comprise any one or more physio-chemical properties, such as: ion mobility; pH; ion size; collision cross section; polarizability; etc.

In an embodiment where the separation device comprises a mass spectrometry imaging device, the separation parameter typically represents a surface location of a sample provided to the mass spectrometry imaging device.

In some embodiments said providing step comprises applying an event detection algorithm to the mass trace, thereby generating an event corresponding to the mass trace, the event comprising the separation parameter centre and the mass centre. Optionally, the event may also comprise any of the following properties or measurements determined by the event detection algorithm: one or more peak widths; a measure of the asymmetry of the peak; a measure of the quality of fit to a model peak; an indication whether the peak is the result of a deconvolution of a plurality of peaks; in indication whether mass corrections where applied; and so on. Additionally, or alternatively said providing step may further comprise providing a separation parameter centre and a mass centre for the mass trace. Such provided separation parameter centre and a mass centre may be those determined by the event detection algorithm.

In a second aspect there is provided a computer implemented method for compressing mass spectrometry data. The method comprises, decomposing the mass spectrometry data into a plurality of mass traces by repeated application of any of the method described above; identifying erroneous mass traces in the plurality of mass traces by applying an event detection algorithm to each of the plurality of mass traces; and forming a compressed version of the mass spectrometry data from the mass traces and the mass spectrometry data corresponding to the identified erroneous mass traces. Typically erroneous mass traces are ones for which the event detection algorithms fails to detect events, and/or fails to fit a pre-defined model peak to the mass trace with above a threshold degree of certainty (or goodness of fit measure).

In some embodiments the compressed version of the mass spectrometry data comprises the mass spectrometry data corresponding to the identified erroneous mass traces, and one or more events generated by the applying of the event detection algorithm in place of the mass spectrometry data relating to the one or more events.

In this way it will be appreciated that the mass spectrometry data has been effectively compressed by replacing parts of the mass spectrometry data with events detected from the plurality of mass traces. For those mass traces which are erroneous, the relevant mass spectrometry data is preserved so that information loss is minimized during the compression.

In some embodiments mass traces of the plurality of mass traces consisting of fewer than a pre-determined number of intensity peaks (or centroids) may be discarded. Optionally, the pre-determined number of intensity peaks may be based on the event detection algorithm. For example, the pre-determined number of intensity peaks may be the minimum number of intensity peaks required by the event detection algorithm to fit to the pre-defined model peak.

The invention also provides apparatus corresponding to, and comprising elements, modules or components arranged to put into effect the above methods, for example one or more various suitably configured computing devices such as those described previously.

In particular the invention therefore provides a system for extracting a mass trace (such as an extracted ion chromatogram) from mass spectrometry data of a mass stream (or ion stream or other stream or flow of analytes) emitted from a separation device as a function of a separation parameter (or separation dimension). The system comprises a receiving module arranged to receive the mass spectrometry data, wherein the mass spectrometry data comprise a plurality of mass spectra each obtained for respective values of the separation parameter; an identification module arranged to identify, from the plurality of mass spectra, a sequence of three or more intensity peaks that are ordered according to the separation parameter. Said identifying the sequence of three or more intensity peaks comprises selecting an initial intensity peak at an initial mass, and for each other intensity peak of the sequence of intensity peaks, selecting said intensity peak based on at least the mass of an adjacent intensity peak in the sequence of intensity peaks; and an output module arranged to provide a mass trace, for a given emitted compound of the mass stream, from the identified sequence of intensity peaks.

Optionally, the system may also be arranged to compress the mass spectrometry data. In particular the system may be arranged to decompose the mass spectrometry data into a plurality of mass traces, and may further comprise an event detection module arranged to identify erroneous mass traces in the plurality of mass traces by applying an event detection algorithm to each of the plurality of mass traces; and a compression module arranged to form a compressed version of the mass spectrometry data from the mass traces and the mass spectrometry data corresponding to the identified erroneous mass traces.

The invention also provides one or more computer programs suitable for execution by one or more processors, such computer program(s) being arranged to put into effect the methods outlined above and described herein. The invention also provides one or more computer readable media, and/or data signals carried over a network, which comprise (or store thereon) such one or more computer programs.

BRIEF DESCRIPTION OF THE DRAWINGS

Embodiments of the invention will now be described, by way of example only, with reference to the accompanying drawings, in which:

FIG. 1c shows two example mass traces as may be generated by the system in FIG. 1a;

FIG. 3a schematically illustrates a logical arrangement of an example analysis system, such as that which may be used in the system in FIG. 1a;

FIG. 3b schematically illustrates a method for obtaining a mass trace from mass spectrometry data that may be carried out (or implemented by) the analysis system of FIG. 3a;

DETAILED DESCRIPTION OF EMBODIMENTS OF THE INVENTION

In the description that follows and in the figures, certain embodiments of the invention are described. However, it will be appreciated that the invention is not limited to the embodiments that are described and that some embodiments may not include all of the features that are described below. It will be evident, however, that various modifications and changes may be made herein without departing from the broader spirit and scope of the invention as set forth in the appended claims.

Figure 1A:
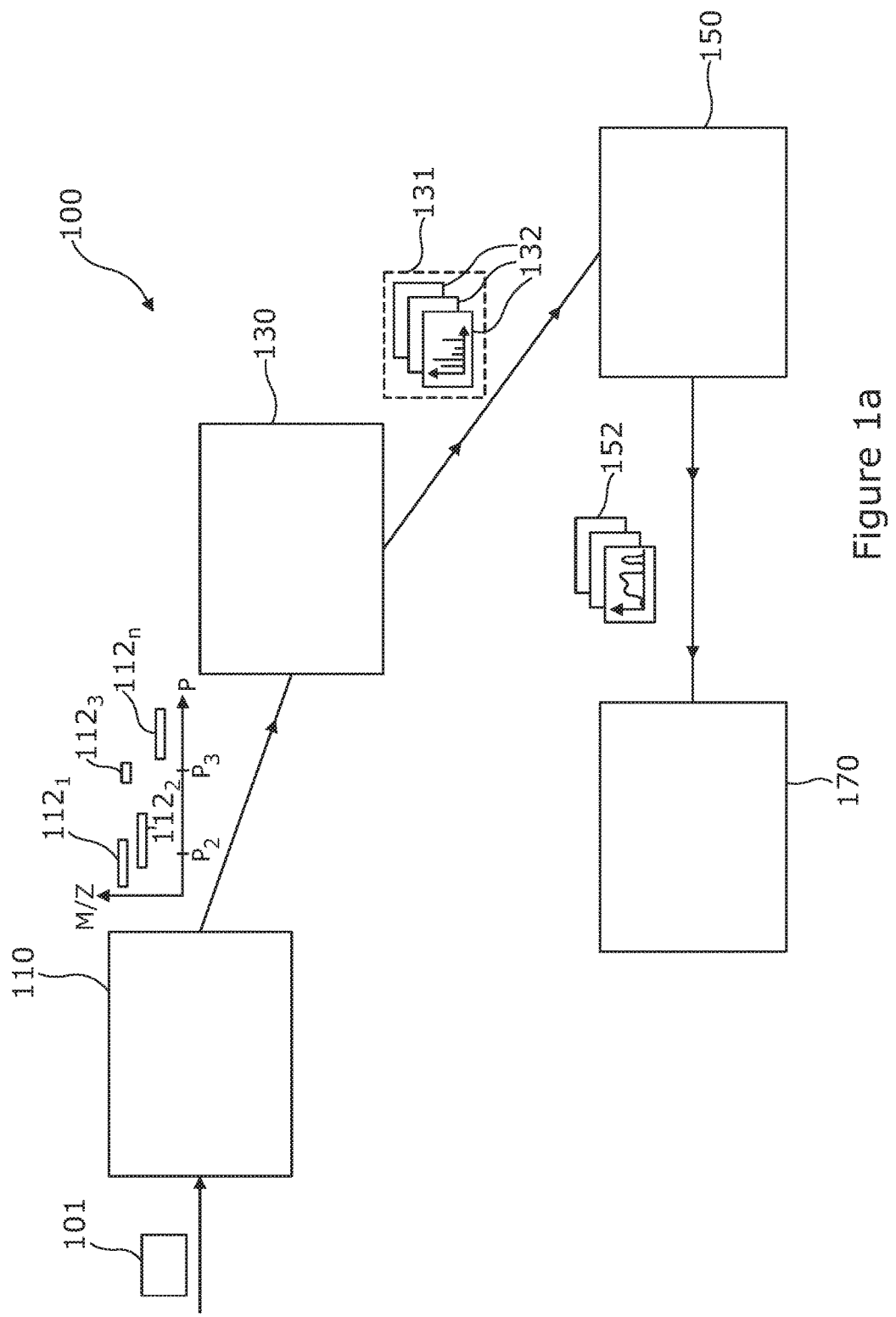
FIG. 1a schematically illustrates an example system for coupled separation/mass spectrometry analysis of a sample.

FIG. 1a schematically illustrates an example system 100 for coupled separation/mass spectrometry analysis of a sample 101. The system 100 is shown as comprising a separation device 110, a mass spectrometer 130, a mass trace analysis system 150, and a further processing module 170.

The separation device 110 is configured to separate a sample 101 into a plurality of components (or analytes) 112. In particular, the separation device 110 is usually configured to cause components (or analytes) 112 to elute (or emit or otherwise emanate) from the separation device 110 as a function of a separation parameter (or dimension). The separation parameter (or parameters) may also be thought of as an elution parameter, especially where the separation device comprises a chromatograph or chromatography column. The analytes are typically emitted by the separation device 110 as a mass stream (or an ion stream), which may then be introduced (or injected) into a mass spectrometer 130 as described shortly below. It will be appreciated that this mass stream may be a continuous flow of various analytes or it may be pulsed depending on the rate at which the analytes are separated from the sample 101.

For example, the separation device 110 may be a liquid (or gas) chromatograph, of the types commonly known in the art. In this example the elution parameter would be retention time. In other words the duration of time needed for the component to pass through the chromatograph (e.g. the time between the sample being injected into the device and the component being provided to the mass spectrometer 130). As liquid (and gas) chromatographs are well known in the art they will not be described further herein.

In another example the separation device 110 may be an imaging device of the type used in mass spectrometry imaging (such as matrix-assisted laser desorption ionization (MALDI), or secondary ion mass spectrometry (SIMS) imaging). In these examples the sample 101 comprises a surface which is scanned, usually by an ionising beam (such as an ion beam or laser). Typically, the ionising beam causes a component (or components) 112 to emanate (or emit) from the position on the surface of the sample 101 on which the beam is focussed. As the beam scans the sample 101 the components 112 are emitted as a function of the scan path. In this way it will be appreciated that the separation parameter may be a coordinate on the surface of the sample 101, or a parameter indicating the scan order of the beam (such as a pixel in a raster scan). As mass spectrometry imaging is well known in the art it will not be described further herein.

Besides the many variants of chromatography and imaging, many other separation devices and methods are known in the art, including ion mobility and differential ion mobility separation, electrophoresis, separation by binding to (elements of) an array of binding agents.

The separation device 110 is coupled to a mass spectrometer 130. In particular, the separation device 110 is configured to provide the emitted components to the mass spectrometer 130. These components 112 are introduced, typically by injection, into the mass spectrometer 130. The mass spectrometer 130 may be arranged to ionise (and optionally fragment) the injected components 112. Alternatively the components 112 provided by the separation device 110 may already be ionised. For example where the separation device 110 is an ion mobility separator or an imaging device (such as in a MALDI device), the components 112 will often be ionised by the separation device 110. In this way it will be appreciated that the separation device 110 may be the ion source of the mass spectrometer 130.

The mass spectrometer 130 is arranged to generate a mass spectrum 132 of relative abundance (or intensity) against the mass-to-charge ratio (i.e. m/z value) of the ionised fragments (or components 112). A mass spectrum 132 is described in further detail shortly below. It is known that the generation of a mass spectrum 132 may involve separation or selection of the ionised components according to their m/z value, followed by the measuring of a signal or signals caused by these separated groups of ions and/or ionised fragments. The separation or selection of the ionised components can happen in that ions of a specific m/z value have specific trajectories, on which these ions oscillate. Due to this oscillation, characteristic signals of the ions can be detected which have a frequency $\omega$ and from which a specific m/z value can be assigned. The operation of mass spectrometers is well known in the art and not described further herein. The skilled person would appreciate that the mass spectrometer 130 may be of any type. For example the mass spectrometer may be any one of: a time of flight (TOF) mass spectrometer, a Fourier transform ion cyclotron resonance mass spectrometer (FT-ICRMS), an Orbitrap™ mass spectrometer etc.

The components 112 are typically received by the mass spectrometer 130 as a function of the separation parameter. In this way it will be appreciated that the mass spectrometer 130 receives components 112 emitted at the same value (or within the same range of values) of the elution parameter simultaneously (or substantially simultaneously). Consequently, the mass spectrometer 130 is arranged to generate mass spectra 132 as a function of the separation parameter. In other words each mass spectrum 132 is generated for a respective value of the elution parameter. More specifically, each mass spectrum 132 may be thought of as (or representing) a mass spectrum 132 of the components 112 emitted at a respective value of the elution parameter. Each mass spectrum 132 need not be a full mass spectrum in the sense of a complete intensity vs m/z plot across the entire m/z range. For example, a mass spectrum 132, as referred to herein, may comprise one or more m/z vs intensity data points. The mass spectrum 132 may be limited to a particular m/z range of interest. In an extreme case a mass spectrum 132 may comprise only the centroids within a particular m/z range of interest.

Thus, it will be understood that the mass spectra 132 form a data set with at least the dimensions of: intensity (or abundance); m/z (or mass); and elution parameter. The mass spectrometer 130, therefore, is arranged to produce mass spectrometry data (or coupled separation/mass spectrometry data) 131. The mass spectrometry data 131 comprises the plurality of mass spectra 132 each obtained for respective values of the separation parameter.

Indeed some devices, such as quadrupole mass spectrometers or some time-of-flight mass spectrometers may not provide mass spectrometry data 131 as an ordered set of plotted mass spectra 132 with respect to separation parameter. Instead the mass spectrometry data may be a stream of m/z-intensity value pairs, with associated values of the separation parameter.

For example a quadrupole mass spectrometer may detect multiple mass ranges in a non-sequential fashion leading to an out-of-order mass to separation parameter relation. Alternatively a Hadamard transform time-of-flight instrument or a similarly operated device may provide a sequence of mass arrival times that requires deconvolution for determination of the parameter of the separation dimension.

It will be understood that such mass spectrometry data may still be said to comprise mass spectra 132 since, as set out above, a mass spectrum 132 may simply be thought of as a data set with the dimensions of intensity (or abundance); m/z (or mass) at a given value (or range of values) of the separation parameter.

It will be appreciated that a given component 112 may emit from the separation device 110 over a range of the separation parameter p. Typically, over this range the abundance of the component 112 may rise to a peak and then fall. However in some cases, such as mass spectrometry imaging, there may be a sharp discontinuity in the abundance of a component. This may be, for example, where the component is present only in a sharply defined area of the sample 101 surface that is scanned by a beam, as described above.

As such, it will be appreciated that in each mass spectrum 132 (or mass spectrum data set 132) in the mass spectrometry data 131, there will be a number of m/z intensity peaks (typically represented as centroids)—i.e. a local maxima in the intensity value with respect to m/z in a single mass spectrum 132. There will also, however, be a number of separation parameter intensity peaks —i.e. local maxima in intensity with respect to separation parameter in the mass spectrometry data 131 for a specific component with its specific m/z value.

The ranges of the separation parameter over which two or more components are emitted may overlap. For example, in a chromatograph, a given component may elute over a period in retention time. In the description that follows, for ease of discussion, examples will typically be given with reference to scenarios involving the use of chromatograms. It will be appreciated, however, that the discussions are not limited to these examples and that discussion involving elution and the elution parameter apply equally to more general separation devices where the terms emitting and separation parameter (or there other alternatives set out above) may be used instead.

For example as shown in FIG. 1a, a first component $112_1$ is first to elute, with respect to the elution parameter. Before the first component $112_1$ finishes eluting with respect to the elution parameter, a second component $112_2$ starts to elute. Thus there is a range of the elution parameter within which both the first component $112_1$ and the second component $112_2$ simultaneously elute, and are thus simultaneously injected into the mass spectrometer 130. A mass spectrum $132_{p_2}$ generated for a value of the elution parameter $p_2$ in this range will include m/z intensity peaks for both the first component $112_1$ and the second component $112_2$.

Conversely, as shown in FIG. 1a, a third component $112_3$ is third to elute, with respect to the elution parameter, and does so whilst no other component 112 is also eluting. Thus, a second mass spectrum $132_{p_3}$ generated for a value of the elution parameter $p_3$ in the range where the third component $112_3$ elutes will include m/z intensity peaks for just the third component $112_3$.

The analysis system 150 is arranged to receive the mass spectrometry data 131 generated by the mass spectrometer 130. The analysis system 150 may be (or comprise) one more computer systems, such as a computer system 200 described in more detail shortly with reference to FIG. 2. The analysis system 150 is arranged to generate one or more mass traces 152, based on the mass spectra 132 in the received mass spectrometry data.

Figure 1B:
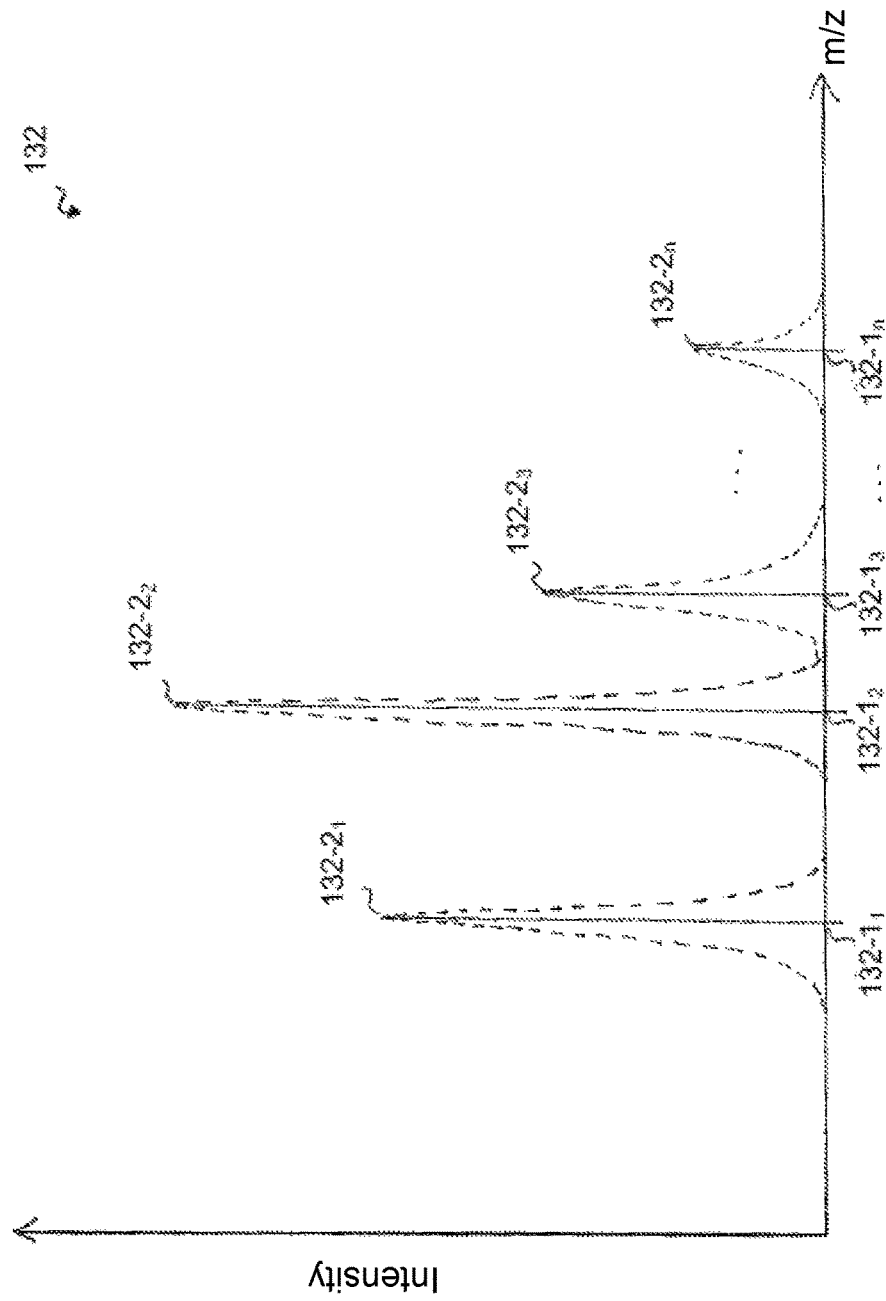
FIG. 1b shows an example graphical representation of a mass spectrum.
Figure 1C:
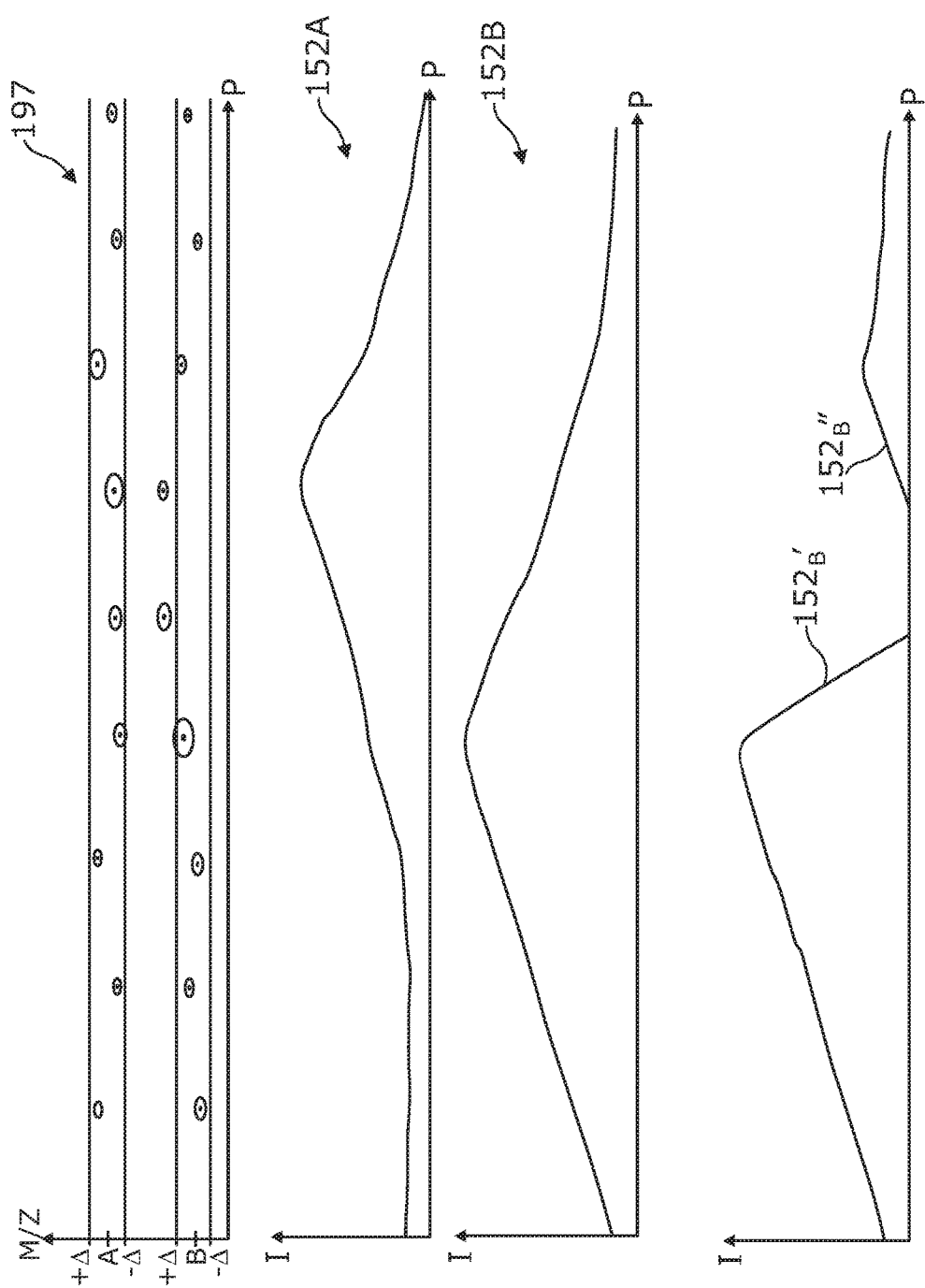

A mass trace 152, such as the example mass trace $152_A$ shown in FIG. 1c, typically comprises a set of m/z intensity (or relative abundances) peaks (or centroids) as a function of the elution parameter, for a particular ion fragment of a component 112 eluted from the sample 101. As each mass spectrum 132 typically corresponds to a respective different value of the elution parameter, each centroid in the mass trace 152 comes from a respective different mass spectrum 132.

One particular example of a mass trace 152, in the case where the separation device 110 is a chromatogram, is an extracted ion chromatogram which is well known in the art.

The further processing module 170 is arranged to receive the generated mass traces 152. The further processing module 170 is then arranged to perform further processing techniques on the mass traces 152 in order to identify particular eluted compounds 112 and/or information regarding the structure and make-up of the sample 101.

Mass traces are often useful for processes such as: the re-examination of data to detect previously-unsuspected analytes; the highlighting of potential isomers, the resolving of suspected co-eluting substances; and the providing of clean chromatograms of compounds of interest.

There are numerous such processing techniques known in the art which rely on accurate mass traces 152, including the Compound Discoverer and Proteome Discoverer software products from Thermo Scientific. In the Proteome and Compound Discoverer products, the mass traces 152 may be used as input for an event (or peak) detection algorithm that determines (or identifies) events of relevance in the data. These events may then be used for a variety of different processes, including: chromatographic alignment, comparison of similar events in different chromatographic runs (for example for determination of the relative amounts and/or presence or absence of certain proteins in different samples), and for the determination of the relative amounts of metabolites of pharmaceutical products formed in an organism under different conditions.

It will be appreciated that improved mass traces 152 typically leads to more correctly recognized chromatographic peaks. This in turn may lead to more correctly identified and quantitated peptides. This is important in many scenarios, for example differential expression experiments where better relative protein quantitation can be obtained. Determining which proteins change in abundance under different circumstances ultimately helps identifying correlations of proteins with states of disease or response to treatment. Thus as a consequence the diagnosis of a state of health of a patient may be improved by improvements of the determination of mass traces. Indeed, without accurate mass trace determination, signals significant for treatment may be irrecoverably lost early on in the data evaluation process, as set out in "Current challenges in software solutions for mass spectrometry-based quantitative proteomics" by Cappadona et al. in Amino Acids (2012) 43:1087-1108.

Another use of mass traces 152 is shown in Biller, J. E. and Biemann, K. (1974) "Reconstructed Mass Spectra, A Novel Approach for the Utilization of Gas Chromatograph—Mass Spectrometer Data", Analytical Letters, 7:7, 515-528. Here mass traces are used to correlate fragment ions with their respective parents in GC-MS. A similar method is discussed in U.S. Pat. No. 9,312,110, where the parent ions are in separately acquired full MS spectra and the fragment ions are acquired in $MS^2$ spectra, which may be generated by many known methods for dissociation of ions.

In the case of mass spectrometry imaging, the mass traces 152 may be processed to identify separate regions on the surface of a sample. Known methods from visual imaging (such as watershed methods), may be used on the mass traces to separate the regions. Additionally it is possible to guide the region separation based on external information, which may for example be derived from optical or electron microscopy of the same sample.

FIG. 1b shows an example graphical representation of a mass spectrum 132.

The mass spectrum 132 comprises one or more m/z values (or mass to charge ratios) $132\text{-}1_i$ (where i is simply an index which runs from 1 to n). Each m/z value corresponds to a respective ionic species and is equal to the molecular mass of the respective ionic species divided by the absolute elemental charge of the respective ionic species. The mass spectrum 132 comprises one or more intensity values $132\text{-}2_i$ with each intensity value $132\text{-}2_i$ appearing for a respective m/z value $132\text{-}1_i$. Each intensity value $132\text{-}2_i$ correlates to the relative abundance of the ionic species corresponding to the respective m/z value $132\text{-}1_i$. Each intensity value $132\text{-}2_i$ may be proportional to the relative abundance of the ionic species corresponding to the respective m/z value.

An experimental mass spectrum such as the mass spectrum 132 may be plotted (or represented) in the form of a continuum plot, indicated by the dashed line, and a centroid plot, indicated by the vertical solid lines. The widths of peaks indicated by the dashed line represent the limit of the mass resolving power, which is the ability to distinguish two different ionic species with close m/z ratios.

However, it will be appreciated that the mass spectrum 132 does not need to be plotted (or stored) in the form of a graph. Indeed, the mass spectrum 132 may be represented in any suitable form. For example, the mass spectrum 132 may be represented as a list comprising the one or more intensity values $132\text{-}2_i$ and the one or more m/z values $132\text{-}1_i$. In some cases, the mass spectrum 132 may simply be represented as a list of centroids (or local maxima), each centroid being represented as an m/z value and intensity value pair.

As there are many techniques commonly used in the art for obtaining such centroids from mass spectrometry data these will not be discussed further herein. However, it will be appreciated that the techniques described herein may be performed on lists of centroids forming mass spectra 132, or on raw mass spectra 132 where suitable techniques are used to identify the intensity maxima (or centroids).

FIG. 1c shows two example mass traces $152_A$; $152_B$ as may be generated by the system 100.

In FIG. 1c there is shown a graph 197 plotting centroids (or intensity peaks) from the mass spectra 132 as the m/z value of each centroid vs. the value of the elution parameter of the mass spectrum 132. Said centroid forms part of the intensity of each centroid is indicated by the diameter of the circle surrounding the point for ease of visualization. As can be seen there are two clear sequences of centroids centred around m/z values A and B respectively, present in the graph 197. These represent the elution of two compounds, one with a signature m/z value of A and another with a signature m/z value of B. As can be seen there is a slight variation of m/z value with respect to elution parameter which is typically caused by the inherent accuracy of the mass spectrometer. This accuracy can vary with respect to the number of ions present in the mass spectrometer, which itself tends to rise and fall over the elution of a given compound.

For both the mass trace $152_A$ for the m/z value of interest A, and the mass trace $152_B$ for the m/z value of interest B, the respective mass trace $152_A$; $152_B$ is a plot of the intensity of the centroids around the respective m/z value of interest, against the value of the elution parameter for those centroids. In the case where the separation technique was a chromatographic technique the elution parameter will be the retention time and the mass trace will be an extracted ion chromatogram for the m/z value of interest.

To account for the slight variation in m/z values, prior art mass trace extraction techniques typically form a mass trace by including all of the centroids with m/z values within a certain range Δ, either side of the m/z value of interest, as shown in FIG. 1c. This range (typically 2Δ) is often known as the mass window (or mass window width) and is predefined, frequently either specified by a user or software architect, or determined programmatically from other information. In particular, the mass window may be generated based on the mass spectrometer type and/or resolution settings. In other words, the mass window is used to take account of the fact that there is a finite accuracy in the m/z values reported by a mass spectrometer, causing variation in reported m/z values from one mass spectrum to the next.

However, it has now been observed that the reported m/z values of two nearby centroids in the same spectrum may be deflected. Typically the centroids are deflected towards each other (or in some case one of the centroids, typically the less intense centroid, is deflected towards the other centroid). However, as the deflection may be due to general effects of interactions of ions within the mass analyzer, the centroids may be deflected away from each other in some cases. In either case, this can lead to some of the centroids being deflected outside of the mass window Δ around the m/z value of interest, as can be seen in the graph 197 in relation to the centroids for the m/z value of interest B. This is despite the fact that those centroids are still related to the signature m/z value of B for the same eluted compound as the centroids within the mass window.

This leads to erroneous mass traces being generated, such as the mass traces $152_{B'}$ and $152_{B'''}$. Here, due to the missing centroids outside of the mass window, two separate mass traces are generated. Each of these two erroneous mass traces has an associated respective peak (or event) in intensity with respect to the elution parameter. In this example, the first peak is located at the same value of the elution parameter as the peak of the true mass trace $152_B$. However, the shape of the first peak differs from that of the true peak. This shape difference, combined with the erroneous second peak may prevent identification of the eluting compound that led to this mass trace. In some cases due to the unusual truncated shape of the two erroneous peaks they may simply be discarded by the analysis system preventing identification of the eluting compound. Alternatively, the two erroneous peaks may lead to a misclassifying of the eluted compound, for example further analysis may assume that the two erroneous peaks were the result of two separately eluting compounds.

Figure 2:
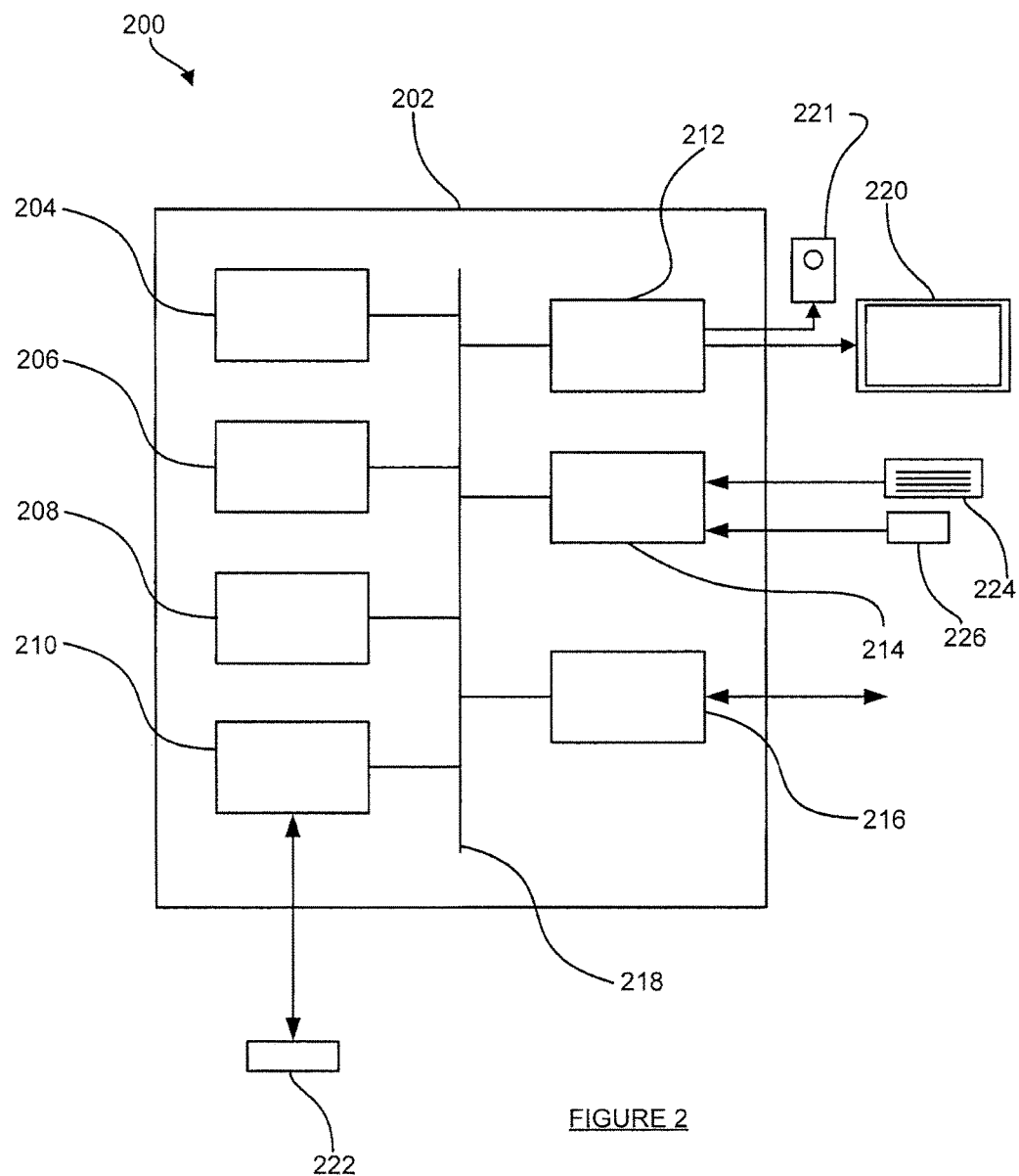
FIG. 2 schematically illustrates an example of a computer system which may be used in the invention.

FIG. 2 schematically illustrates an example of a computer system 200. The system 200 comprises a computer 202. The computer 202 comprises: a storage medium 204, a memory 206, a processor 208, an interface 210, a user output interface 212, a user input interface 214 and a network interface 216, which are all linked together over one or more communication buses 218.

The storage medium 204 may be any form of non-volatile data storage device such as one or more of a hard disk drive, a magnetic disc, an optical disc, a ROM, etc. The storage medium 204 may store an operating system executable by the processor 208. The execution of the operation system by the processor 208 may be required for the computer 202 to function. The storage medium 204 may also store one or more computer programs (or software or instructions or code).

The memory 206 may be any random access memory (storage unit or volatile storage medium) suitable for storing data and/or computer programs (or software or instructions or code).

The processor 208 may be any data processing unit suitable for executing one or more computer programs (such as those stored on the storage medium 204 and/or in the memory 206), some of which may be computer programs according to embodiments of the invention or computer programs that, when executed by the processor 208, cause the processor 208 to carry out a method according to an embodiment of the invention and configure the system 200 to be a system according to an embodiment of the invention. The processor 208 may comprise a single data processing unit or multiple data processing units operating in parallel, separately or in cooperation with each other. The processor 208, in carrying out data processing operations for embodiments of the invention, may store data to and/or read data from the storage medium 304 and/or the memory 206.

The interface 210 may be any unit for providing an interface to a device 222 external to, or removable from, the computer 202. The device 222 may be a data storage device, for example, one or more of an optical disc, a magnetic disc, a solid-state-storage device, etc. The device 222 may have processing capabilities—for example, the device may be a smart card. The interface 210 may therefore access data from, or provide data to, or interface with, the device 222 in accordance with one or more commands that it receives from the processor 208.

The user input interface 214 is arranged to receive input from a user, or operator, of the system 200. The user may provide this input via one or more input devices of the system 200, such as a mouse (or other pointing device) 226 and/or a keyboard 224, that are connected to, or in communication with, the user input interface 214. However, it will be appreciated that the user may provide input to the computer 202 via one or more additional or alternative input devices (such as a touch screen). The computer 202 may store the input received from the input devices via the user input interface 214 in the memory 206 for the processor 208 to subsequently access and process, or may pass it straight to the processor 208, so that the processor 208 can respond to the user input accordingly.

The user output interface 212 is arranged to provide a graphical/visual output to a user, or operator, of the system 200. As such, the processor 208 may be arranged to instruct the user output interface 212 to form an image/video signal representing a desired graphical output, and to provide this signal to a monitor (or screen or display unit) 220 of the system 200 that is connected to the user output interface 212.

Finally, the network interface 216 provides functionality for the computer 202 to download data from and/or upload data to one or more data communication networks.

It will be appreciated that the architecture of the system 200 illustrated in FIG. 2 and described above is merely exemplary and that other computer systems 200 with different architectures (for example with fewer components than shown in FIG. 2 or with additional and/or alternative components than shown in FIG. 2) may be used in embodiments of the invention. As examples, the computer system 200 could comprise one or more of: a personal computer; a server computer; a laptop; a mobile telephone; a tablet; other mobile devices or consumer electronics devices; cloud computing resources; network attached devices; etc.

Figure 3A:
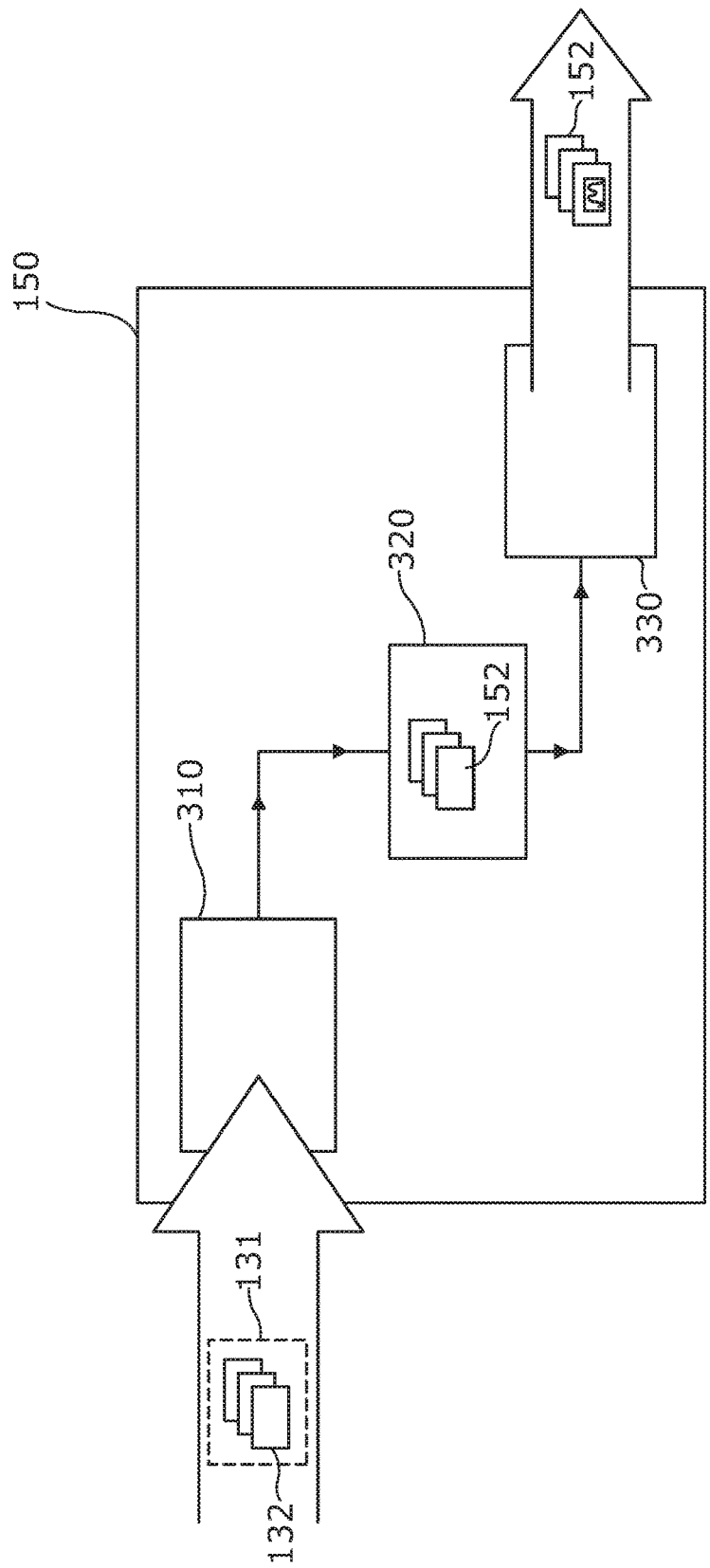

FIG. 3a schematically illustrates a logical arrangement of an example analysis system 150, such as that which may be used in system 100. The analysis system 150 comprises a receiver module 310, a mass trace generation (or extraction) module 320, and mass trace processing module 330.

The receiver module 310 is arranged to receive mass spectrometry data 131. Typically, the receiver module 310 is arranged to receive the mass spectrometry data from a mass spectrometer coupled to (or connected to) the analysis system 150. However, it will be appreciated that the receiver module 310 may be arranged to receive the mass spectrometry data 131 from any suitable source, including a data storage device, a cloud computing service, a test data generation program etc. As set out previously, the mass spectrometry data 131 comprise a plurality (or series) of mass spectra 132 generated by a mass spectrometer 130 in dependence on an elution parameter (such as retention time).

The mass trace generation module 320 is arranged to extract (or obtain) one or more mass traces 152, based on the received mass spectra 130. In particular, the mass trace generation module 320 is arranged to identify a sequence, ordered according to the elution parameter, of three or more intensity peaks from the mass spectra of the received mass spectrometry data 131. As part of identifying the sequence, the mass trace generation module 320 is usually arranged to select an initial intensity peak from the mass spectra 132. The initial intensity peak may be selected based on an m/z value (or range) of interest. It will be appreciated that such an m/z value (or range) of interest may be specified in many different ways, such as by a user, by other analysis of the mass spectrometry data 131, based on known properties of the sample 101 etc. As set out shortly below, the initial intensity peak may be selected based on a sampling of the mass spectrometry data 131. Beginning with the initial intensity peak, the mass trace generation module 320 is arranged to select the further intensity peaks of the sequence by following (or tracking) the mass trace, as a function of the elution parameter. In other words the mass trace generation module 320 is arranged to, for each further intensity peak of the sequence of intensity peaks, select said further intensity peak based on an adjacent already selected intensity peak in the sequence.

The mass trace processing module 330 is arranged to provide the extracted one or more mass traces 152. Usually the mass trace processing module 330 is arranged to plot the intensity of the sequence of centroids as a function of the elution parameter. It will be appreciated that such a plot is not limited to a graphical representation and may include any of a list of coordinate (or plotted points); one or more parameterized curves representing the intensity of the sequence of intensity peaks as a function of the elution parameter; and so on.

The mass trace processing module 330 may be arranged to determine (or calculate or otherwise estimate) a mass centre for an extracted mass trace 152. The mass centre is typically an average of the individual m/z values (or mass values) of the intensity peaks that make up the mass trace 152. In particular the mass centre may be an average of the individual m/z values (or mass values) of the intensity peaks weighted by intensity. Additionally, or alternatively, the intensity peaks may be weighted by signal to noise ratio. Additionally, or alternatively, the deflected centroids may be omitted from the mass centre to provide a corrected mass centre. An example of such mass centre correction is given in "NeuCode labels for relative protein quantification", by Merrill et al. in Mol. Cell. Proteomics, 13 (2014), pp. 2503-2512 which is incorporated herein by reference in its entirety.

As such it will be appreciated that the mass centre for a mass trace 152 is effectively the measured m/z (or mass) value for the (or each) component detected in the mass trace.

Additionally, or alternatively, the mass trace processing module may be arranged to determine an elution parameter centre (such as a retention time centre, or a spatial time centre) for the extracted mass trace 152. Usually, the elution parameter centre is the value of the elution time at which the intensity of the mass trace 152 is highest—i.e. a (typically local) maximum. Such an elution parameter centre may be determined by applying a peak detection algorithm to the mass trace, to determine the peak in an intensity vs elution parameter plot. In an example, the elution parameter centre may be set as the value of the elution parameter that equipartitions the peak area. In higher dimensions this may be equivalent to the geometric centre. It will be appreciated that such an approach may be particularly useful for peaks that do not fit a certain pre-defined model or peak shape. This can often be the case in imaging mass spectrometry.

A combination of a mass centre and an elution parameter centre typically corresponds to an event. Such events are usually the elution of a particular compound. For example, where the mass trace 152 is an extracted ion chromatogram, the mass centre and retention time centre would correspond to a chromatographic event—i.e. the elution of a particular compound having the mass centre as a signature mass from the chromatograph. Events may be identified as a peak in intensity of the mass trace. Alternatively an event detection algorithm may be used which requires other conditions to be satisfied of such a mass trace intensity peak before classifying the peak as an event. For example, the event detection mechanism may require the peak having any one or more of: a minimum area, a minimum conformance to a model peak and or to expected statistical variations, and co-elution with one or more peaks with the same (or substantially the same) value of the elution parameter. Typically, event detection, therefore, comprises peak detection as set out above (usually with each qualifying peak making up an event).

It will be appreciated by a person skilled in the art that there are many known methods for detecting peaks and/or events. In one example a Gaussian curve of the form $He^{-(t-RT)^2/2W^2}$ is fitted to a mass trace 152 using a suitable fitting algorithm (such as a least squares fit). Such a fit would give the intensity of the chromatographic peak of the mass trace as H, the elution parameter centre of the peak as RT, along with the peak width as W.

An overview of peak fitting is given in Data Handling in Science and Technology; Chapters 8 and 11; Volume 21, (1998); Data Analysis and Signal Processing in Chromatography; Edited by Attila Felinger which is incorporated herein by reference in its entirety. The elution parameter centre for an event or peak, such as that described above, may be determined as part of the event, or peak detection algorithm. For example, "Quantification and deconvolution of asymmetric LC-MS peaks using the bi-Gaussian mixture model and statistical model selection" by Yu and Peng in BMC Bioinformatics. 2010 Nov. 12, which is incorporated herein by reference in its entirety, suggests peak detection, and subsequent determination of peak centres (such as elution parameter centres) by fitting a bi-Gaussian model to XICs. Such a method is also an example of one that may be used to detect multiple peaks that may be present in the same mass trace (or XIC).

Given such event detection algorithms are well known in the art they will not be discussed in further detail here. However, it will be understood that the mass trace processing module 330 may be arranged to apply an event detection algorithm and provide one or more detected events for a given extracted mass trace.

The mass trace processing module 330 may also be arranged to calculate other parameters or properties of an extracted mass trace 152. Such other parameters may include any one or more of: signal-to-noise ratios (or measures) for the mass trace 152, a measure of the background noise in intensity for the mass trace 152, one or more peak widths for the mass trace. In particular, it will be appreciated that a peak width for the mass trace 152 may be a width in respect of the m/z dimension (such as a variance of the m/z values of the centroids in the mass trace 152). Additionally, or alternatively, peak width for the mass trace may be a width in respect of the elution parameter dimension.

Figure 3B:
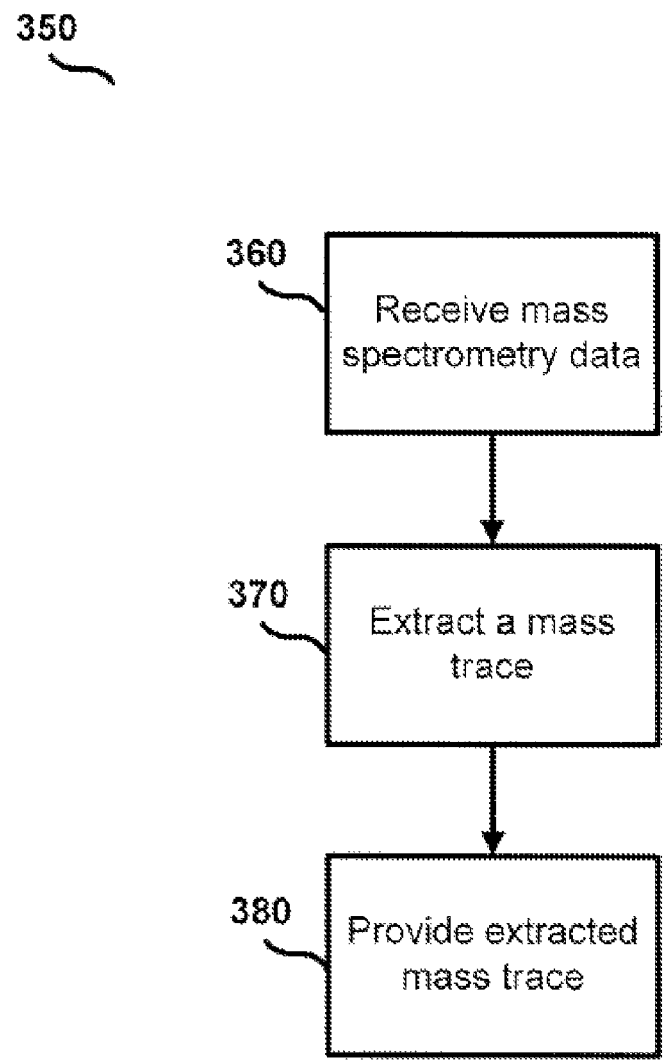

FIG. 3b schematically illustrates a method 350 for obtaining a mass trace 152 from mass spectrometry data 131 that may be carried out (or implemented by) the analysis system 150.

A step 360 comprises the receiver module 320 receiving mass spectrometry data 131 comprising a plurality of mass spectra 132 each obtained for respective values of an elution parameter.

A step 370 comprises the mass trace generation module 320 extracting a mass trace 152, based on the received mass spectra 132. The step 370 comprises the mass trace generation module 320 identifying a sequence of three or more intensity peaks from the plurality of mass spectra 132, the sequence of intensity peaks being ordered according to the elution parameter. In particular, an initial intensity peak at an initial m/z value is selected from the mass spectra 132. For each other intensity peak of the sequence of intensity peaks, said intensity peak is selected based on the m/z value of an adjacent intensity peak in the sequence of intensity peaks A step 380 comprises the mass trace processing module 330 providing the extracted mass trace 152. The step of providing may comprises any one or more of: display of the mass trace 152; storage of the mass trace 152; transmission of the mass trace 152 (such as to a downstream system or processing method), and so on. Optionally, the step 380 comprises the mass trace processing module 330 calculating one or more of: a respective mass centre for the extracted mass trace 152; a separation parameter centre for the extracted mass trace 152 (for example an elution parameter centre); a signal-to-noise ratio for the mass trace 152; a measure of the background noise (typically a background intensity) for the mass trace 152; one or more peak widths for the mass trace 152; a measure of the asymmetry of the peak; a measure of the quality of fit to a model peak; an indication whether the peak is the result of a deconvolution of a plurality of peaks; in indication whether mass corrections where applied; and so on. Any or all of these optionally calculated parameters or properties may be provided with the mass trace 152 as part of the step 380.

It will be appreciated that the steps 370 and 380 may be repeated for the same mass spectrometry data 131, for example to extract a plurality of mass traces 152 for different m/z values of interest. It will also be appreciated that the step 370 may be repeated in order to extract a plurality of mass traces 152, and that the step 380 may be performed a single time in respect of the extracted mass traces 152.

Typically, the step 370 is performed for each intensity peak in the first (or initial with respect to the elution parameter) mass spectrum 132 of the plurality of mass spectra, which has an intensity peak. In other words a mass trace 152 is started for each intensity peak in such first mass spectrum 132. The mass spectra are then usually considered sequentially and a new mass trace started for any further intensity peak which does not form part of an existing extracted mass trace—i.e. the step 370 is also performed for each intensity peak in the subsequent mass spectra which is not part of an existing mass trace 152. In this way it can be assured that as many mass traces 152 are extracted as possible, and that every intensity peak in the mass spectra is considered for inclusion in a mass trace.

Figure 4:
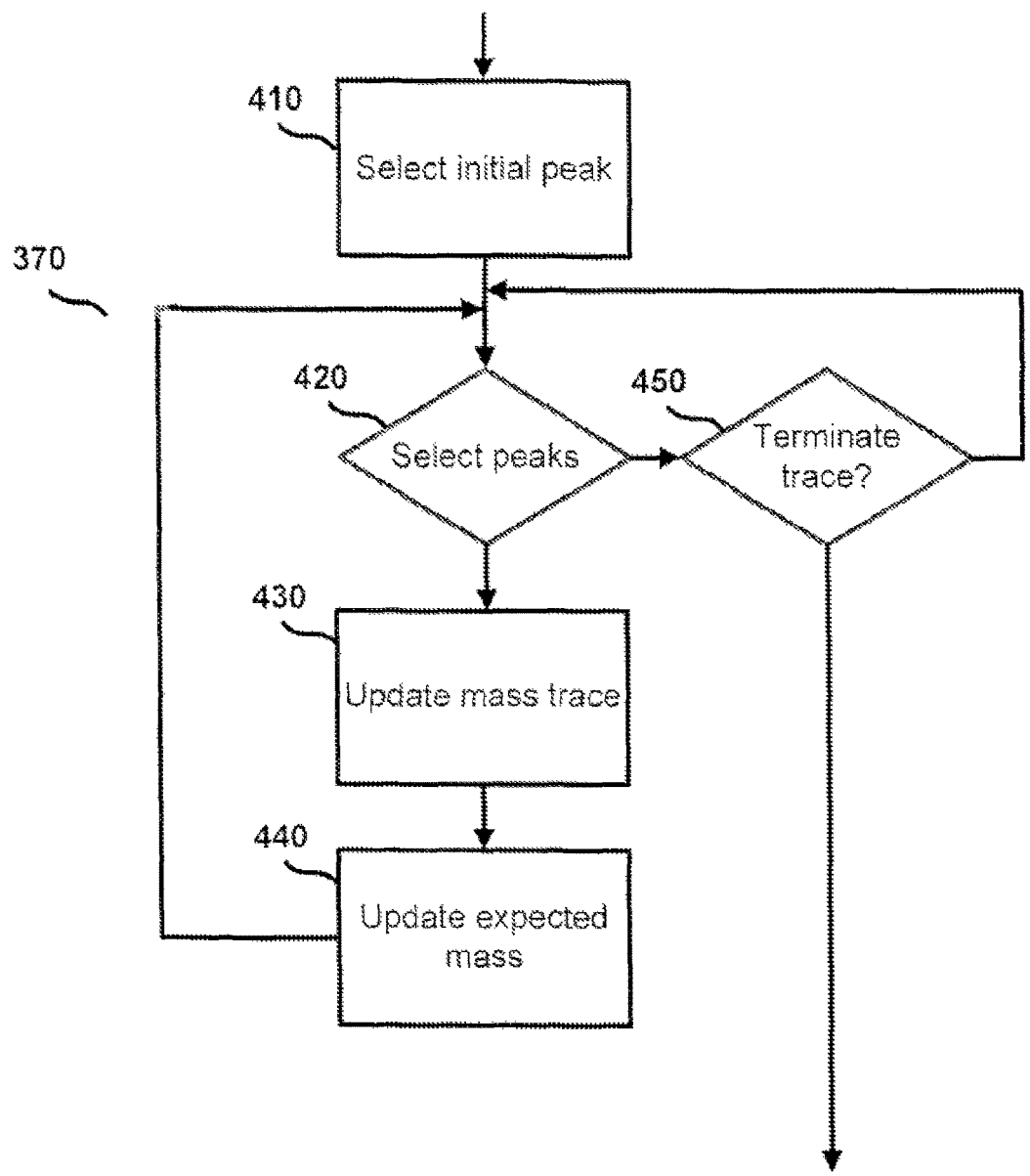
FIG. 4 is a flow diagram schematically illustrating an example implementation of a mass trace generation step for use in the method shown in FIG. 3b.

FIG. 4 is a flow diagram schematically illustrating an example implementation of a mass trace generation step 370 for use in the method shown in FIG. 3b.

A step 410 comprises selecting an initial intensity peak at an initial m/z value of a mass spectrum 132. Often, as set out above, the step 370 is performed multiple times on the same mass spectrometry data 131. In particular, for a given mass spectrum 132 an attempt at extracting a mass trace 152 may be made for each intensity peak (or centroid) in the mass spectrum 132. As such the initial intensity peak may simply be selected in this manner. Additionally, or alternatively one or more m/z values of interest may be specified by a user. The initial intensity peak may be selected based on the one or more m/z values of interest. For example the intensity peak that has the closest m/z value to the m/z value of interest may be selected. Also at the step 410 an expected m/z value is set based on the m/z value of the initial intensity peak. Typically, the expected m/z value is set equal to the m/z value of the initial intensity peak.

It will be appreciated that there are many known ways to select an initial peak for the purposes of generating a mass trace. Typically, a pre-determined intensity threshold is used and an intensity peak in excess of the threshold is selected. Advantageously the peak picking may use the phase of peaks and thresholds are dynamically determined relative to the noise background in the spectra and the background information is preserved. Such methods are set out in U.S. Pat. No. 7,962,301 which is incorporated herein in its entirety. Additionally, or alternatively properties of the mass analyzer may be exploited to reduce the false negative rate, for example as shown, for FT/MS instruments, in U.S. Pat. No. 7,987,060 which is incorporated herein in its entirety.

A step 420 comprises selecting one or more intensity peaks in the next mass spectrum 132 that have an m/z value within a m/z range (or mass tolerance) of the expected m/z value. Typically, the step 420 comprises determining (or identifying) whether one or more intensity peaks in the next mass spectrum 132 have an m/z value within a predefined range of the expected m/z value. This m/z range may be (or comprise) the mass window as described previously. In this way it will be appreciated that the predefined range may be constant over the step 370. Alternatively the predefined range may vary over the step 370, as set out shortly below. In the case where more than one intensity peak is identified in the step 420, the step 420 may comprise selecting all of the intensity peaks. Alternatively, the step 420 may comprise selecting one of the intensity peaks to include in the sequence of intensity peaks. Such selecting may comprise selecting the intensity peak that has the nearest m/z value to the expected m/z value of interest. Alternatively, the selecting may be based on the expected m/z value (or values) of interest of one or more adjacent mass traces 152. For example, intensity peaks that have an m/z value nearer to the expected m/z value of an adjacent mass trace 152 than to the expected m/z value of the current mass trace 152 may be discarded. Then, from the remaining identified intensity peaks the intensity peak that has the nearest m/z value to the expected m/z value of interest may be selected. In the case where all of the identified intensity peaks have been discarded in this way the control flow moves to the "no" branch which is described shortly below.

If one or more intensity peaks in the next mass spectrum 132 having an m/z value within a predefined range of the expected m/z value are selected, then the control flow moves to a step 430.

The step 430 comprises including in the sequence of intensity peaks the intensity peak selected in the step 420. In the case that more than one intensity peak was selected by the step 420 an average intensity peaks based on the selected intensity peaks may be included in the sequence of intensity peaks. Additionally, or alternatively all selected peaks may be included in the mass trace.

A step 440 comprises updating the expected m/z value based on at least the m/z value of the intensity peak included in the sequence of intensity peaks in the step 430. In some cases, the expected m/z value may be set to the m/z value of the intensity peak included in the sequence of intensity peaks in the step 430. Typically, the expected m/z value is updated based on (or to be or to be proportional to) an average of the m/z values of the previous intensity peaks in the sequence. The average may be a windowed average where only the m/z values of a pre-defined number of previous intensity peaks are included. The average may, additionally or alternatively, be a weighted average, such as an average weighted by intensity.

Following the step 440 the control flow then moves back to the step 420. Thus it will be appreciated that an intensity peak identified in the step 420 is identified based on at least the m/z value of an adjacent intensity peak in the sequence of intensity peaks.

If, following the step 420, no intensity peaks have been selected by the step 420 then the control flow moves to a step 450.

The step 450 comprises determining if the mass trace 152 should be terminated. Typically, the mass trace 152 will be terminated if, for a predefined number of consecutive mass spectra, no intensity peaks have been selected by the step 420. Typically, this indicates that the elution of the compound associated with the mass trace has finished. It will be appreciated that other termination criteria may be used. The termination criteria may include predefined and/or dynamically determined criteria in the separation dimension. The termination criteria may include: when the length of the total trace (in the separation dimension) exceeds a multiple of the average expected peak width in the separation dimension. In that case, it will be appreciated that it may be expedient to open a new trace with the latest intensity peak being used as the initial intensity peak of the new trace. In imaging scenarios, it will be appreciated that the scan may be performed in rows. Here the end of a row may terminate a trace. The termination criteria may depend on the number of intensity peaks already selected as part of the sequence, for example the longer the mass trace the greater the predefined number may be. In this way, it will be appreciated that longer mass traces may be more tolerant of gaps or missing intensity peaks then shorter mass traces.

If step 450 determines that the mass trace should not be terminated, then the control flow moves to the step 420 which is carried out for the next mass spectrum in the sequence. It will be appreciated that step 450 may be omitted if the termination criteria require the mass trace to be terminated as soon as no intensity peak is selected in the step 420. In this case the step 370 will terminate directly once no intensity peak is selected in the step 420.

Figure 5:
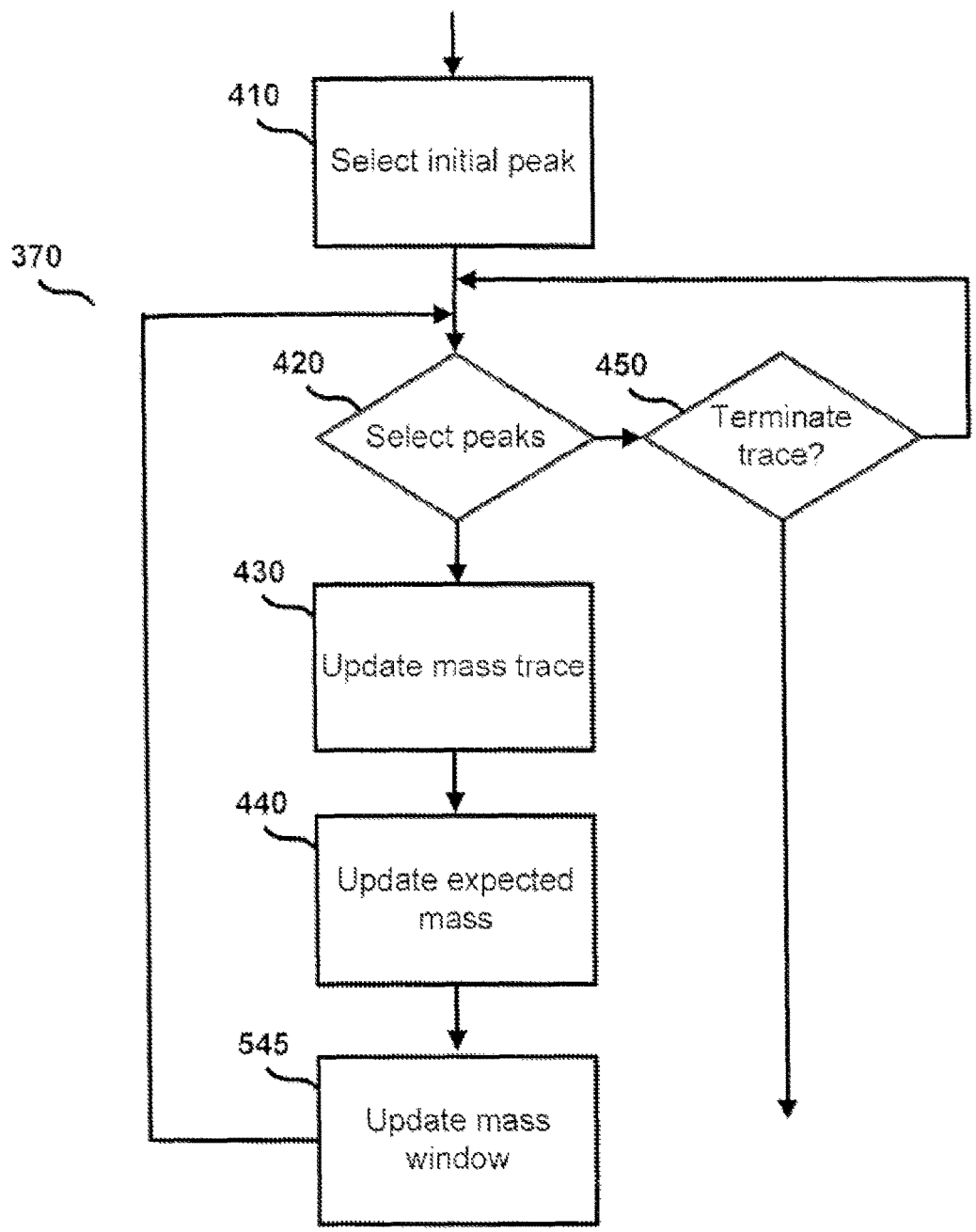
FIG. 5 is a flow diagram schematically illustrating a variant of the example implementation of a mass trace generation step set out in FIG. 4.

FIG. 5 is a flow diagram schematically illustrating a variant of the example implementation of a mass trace generation step 370 set out in FIG. 4. The above discussion of FIG. 4 applies to FIG. 5 except in the following respect.

A step 545 comprises updating the m/z range (or mass window). The m/z range may be updated based on (or be proportional to, or a function of) any of (or any combination of): the resolving power of the mass spectrometer; the expected m/z value; the intensity of the previously selected intensity peak in the sequence; the signal to noise ratio; and so on. Typically, the m/z range will not be updated to be below 0.1 ppm with respect to the expected m/z value. It will be appreciated that in some examples the m/z range may be dependent (or be determined based on) neighbouring (or adjacent) peaks in in the same mass spectrum (i.e. peaks adjacent in the m/z dimension). For example, if a neighbouring peak is close enough in the m/z dimension to the expected m/z value to cause an "attraction" towards the neighbouring peak, then the mass window may be adjusted to take account of said predicted "attraction". Such adjustment may include widening the window and/or shifting the window towards the neighbouring peak. By tracking the mass variation in all mass traces the mass window may be adjusted based on automatically observed trends. For example, a mass window may be functionally dependent on mass and/or intensity. In particular, it will be appreciated that lower ions detected by the mass spectrometer with a lower signal-to-noise ratio will show higher mass variability due to the influence of noise. Thus, the m/z range may be made inversely dependent on the signal-to-noise ratio.

It will be appreciated that the step 410 may comprise setting the m/z range based on the m/z value of the initial intensity peak in a similar manner to step 545 above.

In the example implementation of the method shown in FIG. 5 the following criteria and parameters may be used.

The expected m/z value set in the step 410 and 440 is equal to avg_mz which is the average m/z value of the four previously selected intensity peaks in the sequence. Where fewer than four intensity peaks in the sequence have been previously selected all of the previously selected intensity peaks in the sequence are used.

The mass tolerance is tol_amu=MINIMUM(2avg_mz/res*2/3, 1.5*avg_mz/1e6). The factor of 1.5 may typically be substituted for values between 0.1 and 100. Values close to 0.1 would be most suitable for ultra-high resolution FTMS, whereas values around 100 would be most suitable for time-of-flight mass spectrometry. res is set equal to the ratio of the m/z value to the full width half maximum (FWHM) value of the intensity peak—i.e. res=m/z/FWHM.

The predefined number (or maximum gap length) for determining whether or not to terminate the mass trace is maxGapLen=MAXIMUM(len/3, 10) where len is the number of intensity peaks in the sequence when the test is applied. It will be appreciated that the maximum maxGapLen (here set as 10) may be dynamically determined. In particular the maximum maxGapLen may be dynamically determined, based on any of: instrument-type, signal to noise ratio, an observed (or pre-set) chromatographic peak width; etc. Typically a reasonable range is somewhere between 3 to 10 or the average peak width in the used separation method.

The example method is illustrated by the pseudocode given below:

```
FOR EACH (mass spectrum (elution parameter ascending
   order) )
   FOR EACH ( active mass trace (mass ascending order) )
      FOR EACH ( centroid in mass spectrum (mass
         ascending order) )
         IF (mass centroid is below avg_mz − ½ *
            tol_amu )
            No match found: Add centroid to new mass
            trace as initial intensity peak
            CONTINUE     (Continue with next mass
                          centroid)
         ELSE IF( mass centroid is above avg_mz + ½ *
            tol_amu )
            No match found: Add centroid to new mass
            trace as initial intensity peak
            BREAK        (Continue with next auto
                          trace)
         ELSE
            Check whether this or the next mass
            trace has a smaller match to the current
            mass centroid. Assign mass centroid to
            the mass trace with smaller distance
      END centroid
      IF ( no mass centroid was assigned to current mass
         trace )
         Add gap (zero mass centroid) to mass trace
         IF ( maxGapLen points reached )
            terminate mass trace and provide
            terminated mass trace
   END mass trace
END mass spectrum
```

Figure 6A:
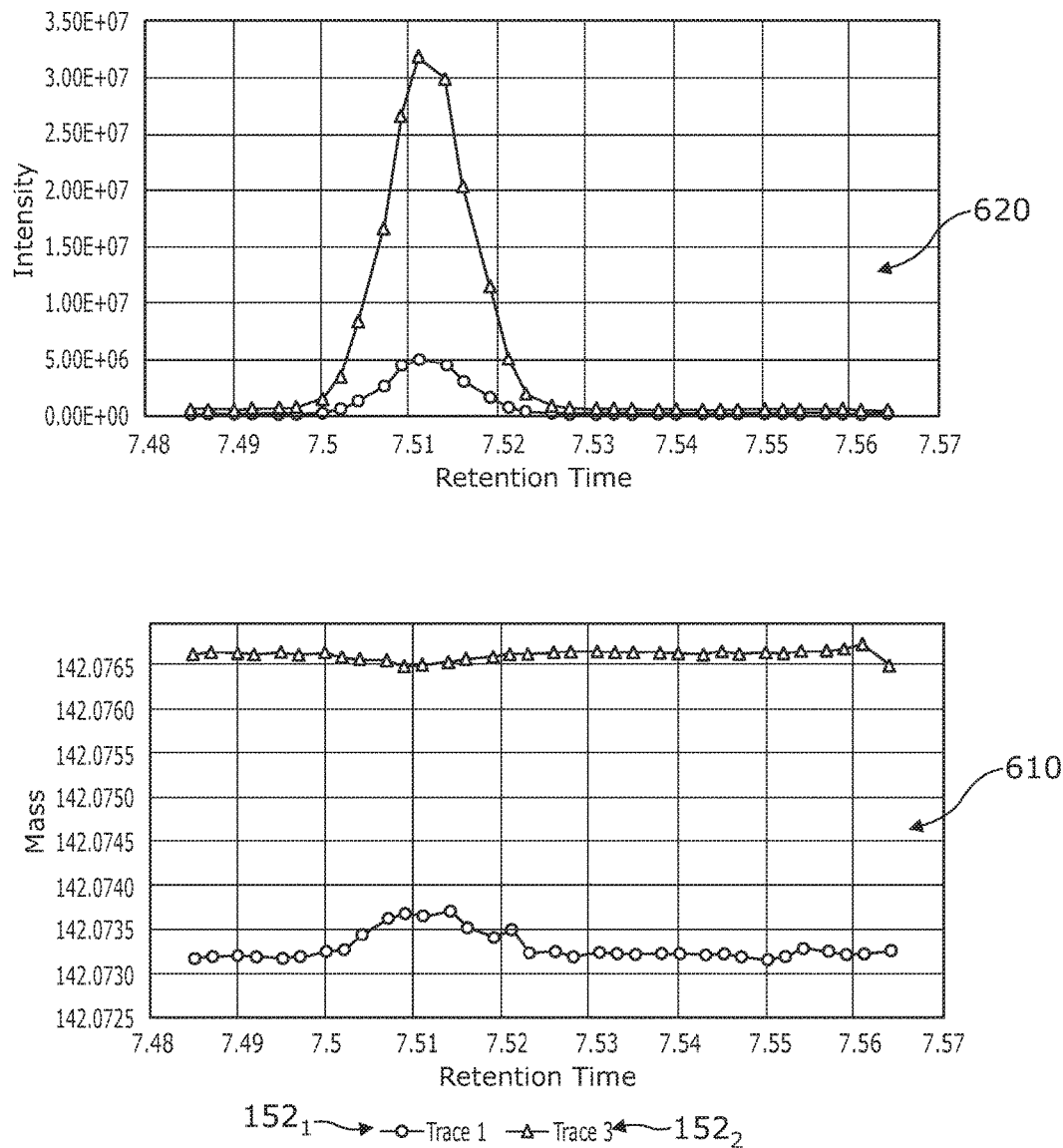
FIG. 6a shows two graphs with data from an LC-OrbitrapMS data acquisition with mass traces generated using a method, such as that according to FIG. 5.

FIG. 6a shows two graphs with data from a data acquisition LC-Orbitrap® MS system. The graph 610 is a graph 610 plotting centroids (or intensity peaks) of two mass traces $152_1$; $152_2$ as generated by a methods of the invention. As can be seen there are two clear separated mass traces $152_1$; $152_2$, here centred near mass values 142.0765 and 142.0730 respectively, The graph 620 shows the corresponding intensity vs retention time plot of the two mass traces $152_1$; $152_2$.

It can be seen that the lower mass drifts significantly to the higher mass when the intensity increases. The higher mass is also slightly shifting, but the shift is much less pronounced.

It can also easily be seen that there are enough data points in the vicinity of the peak centres to determine the correct, un-shifted masses. In this special cases, where more unaltered data points then shifted data points exist a simple median would already give a significantly improved result for the mass of the lower trace.

A conventional prior art method with a narrow mass extraction window would not pick up the lower mass trace $152_1$ correctly as the sequence of intensities around the retention time 7.51 would fall outside of the mass window. This can be seen in FIG. 6b, a figure analogous to FIG. 6a above but produced using a mass trace detection method of the prior art. As can be seen from FIG. 6b event detection methods applied to the mass trace $152_1$ would be bound to fail, as the actual chromatographic intensity peak is missing from the mass trace $152_1$.

Figure 6B:
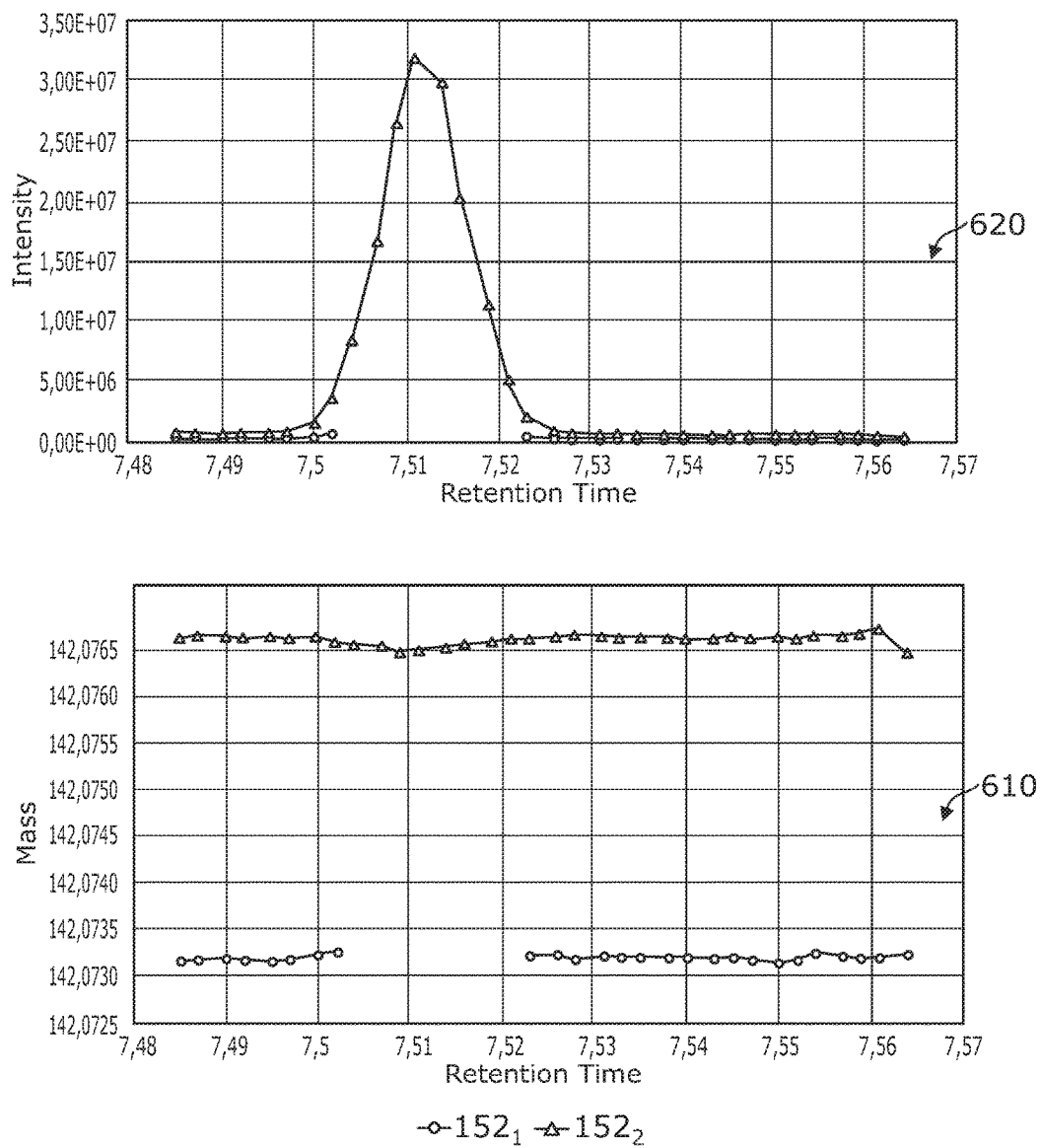
FIG. 6b shows two graphs with data from an LC-OrbitrapMS data acquisition with mass traces generated using a method according to the prior art.
Figure 6C:
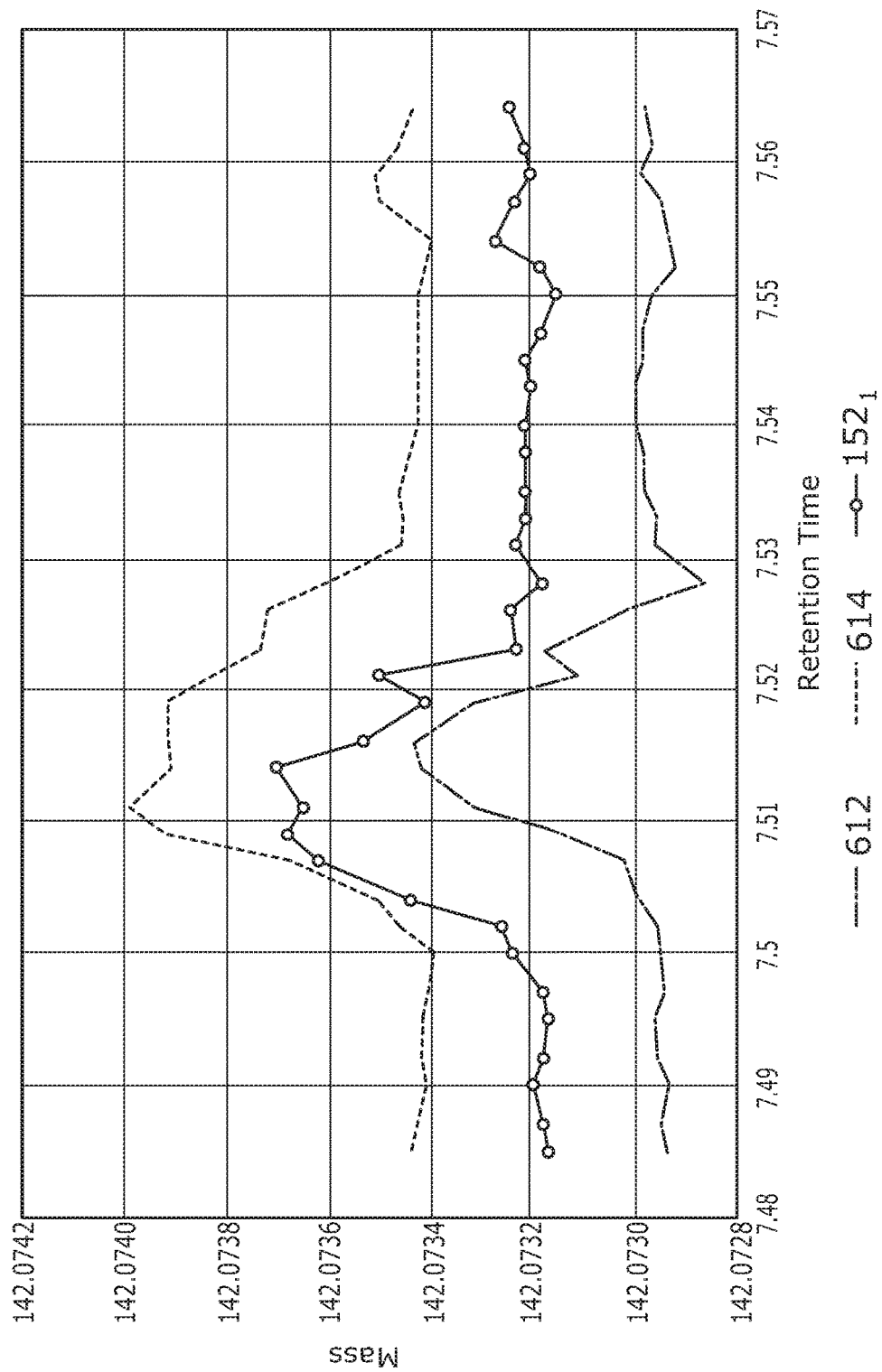
FIG. 6c shows the mass trace from FIG. 6a along with the varying mass range.

FIG. 6c shows the mass trace $152_1$ from FIG. 6a along with the varying mass range.

The line 612 shows the lower bound of the mass range, such as that given by tol_amu as set out above, as it changes along the separation parameter (or retention time in this case). Similarly, the line 614 shows the lower bound of the mass range, such as that given by tol_amu as set out above, as it changes along the retention time.

As can be seen from the lines 612; 614 the range in which the method of the invention is looking for further centroids in the mass trace $152_1$ effectively tracks the mass trace $152_1$. In this way, it can be seen that the method automatically accounts for the large deflection in the mass trace $152_1$ around the retention time 7,51, such centroids fall outside of the expected mass range. Thus no centroids are erroneously omitted from the mass trace 1511 in contrast to the method of the prior art as shown in FIG. 6b above.

The methods described above with reference to FIGS. 3b, 4, and 5 are logically described, for ease of understanding, from the point of view of extracting a single mass trace at a time. This may be considered as mass trace by mass trace type. It will be appreciated, however, that the present invention is not limited to such an implementation. Alternatively, the methods above may be implemented as a centroid by centroid type. In other words, two or more (or all) of the mass traces 150 may be extracted in parallel.

In one example of such a centroid by centroid type, the mass spectra 132 may be considered in order of separation parameter. For a given mass spectrum 132, each centroid in the mass spectrum 132 may be tested, as per step 420, for each of the active mass traces 152 (mass traces 152 that have not been terminated). If the centroid is selected for a given mass trace, the centroid is added to that mass trace 152 (as per step 430) and the expected m/z value, and optionally, the m/z range is updated for that mass trace 152. If a centroid is not selected for any active mass trace 152, then a new mass trace 152 may be started using said centroid as the initial intensity peak. Once all of the centroids for the mass spectrum 132 have been considered then the termination criteria is applied to the active mass traces 152 for which no new centroid has been added. Any mass traces fulfilling the termination criteria are not considered further and may be provided to the mass trace processing module 330. The process is then repeated for the centroids in the next mass spectra (in order of separation parameter).

It will be appreciated that the preceding discussion is not limited to selecting intensity peaks in any particular direction (or sense) of the separation parameter. Whilst it is straightforward to visualize the initial intensity peak being at one point value of the separation parameter and subsequently selected intensity peaks being at subsequent values of the separation parameter it is possible to select an initial intensity peak at a high value of the separation parameter and select further peaks going backwards with respect to the separation parameter. It will also be appreciated that further peaks can be selected moving out from the separation parameter value in any direction. For example, in mass spectrometry imaging a mass trace may be followed along a diagonal on the surface of the sample.

Additionally, or alternatively a mass trace could be followed both forwards and backwards from a given initial intensity peak, with respect to the separation parameter.

Indeed, it may be advantageous to re-follow a mass trace backwards once an average mass (or mass centre) has been determined. This may advantageously improve the selection of the initial intensity peak and may lead to the inclusion in the mass trace of preceding peaks that would otherwise not have been considered part of the mass trace. It will also be appreciated that while chromatographic peaks do not tend to be symmetrical in time, it may still appropriate to use the same selection and termination criteria as when moving forward in time.

It will be appreciated that mass spectrometry data 131, such as that produced by the combined separation mass spectrometry techniques discussed previously, may require large amounts of storage space. For example, a Fourier transform type mass spectrometer may acquire information at a rate of 5 acquisitions (or mass spectra) per second, with each acquisition producing 2 megabytes of data. This can give rise to a data stream of around 100 Mbit/s or a storage requirement of 3.5 gigabytes per hour. This is a common amount of raw data for a single LC/MS experiment.

Additionally, it can often be the case that the further processing of such mass spectrometry data 131, such as that carried out by the further processing module 170 described previously in relation to FIG. 1a, is performed by servers remote to the mass spectrometry device 130 itself. Such remote servers may be connected to the mass spectrometry device 130 via a network, such as the Internet and/or any other suitable local area or wide area network. Indeed, the further processing of such mass spectrometry data 131 may be carried out using cloud computing resources and/or other such software as a service (SaaS) architectures. Typically, the mass trace generation is performed by the same remote processing system, necessitating the entire mass spectrometry data to be transmitted to the remote systems (or cloud computing systems). Thus large amounts of bandwidth are required for the transmission for the mass spectrometry data.

Figure 7:
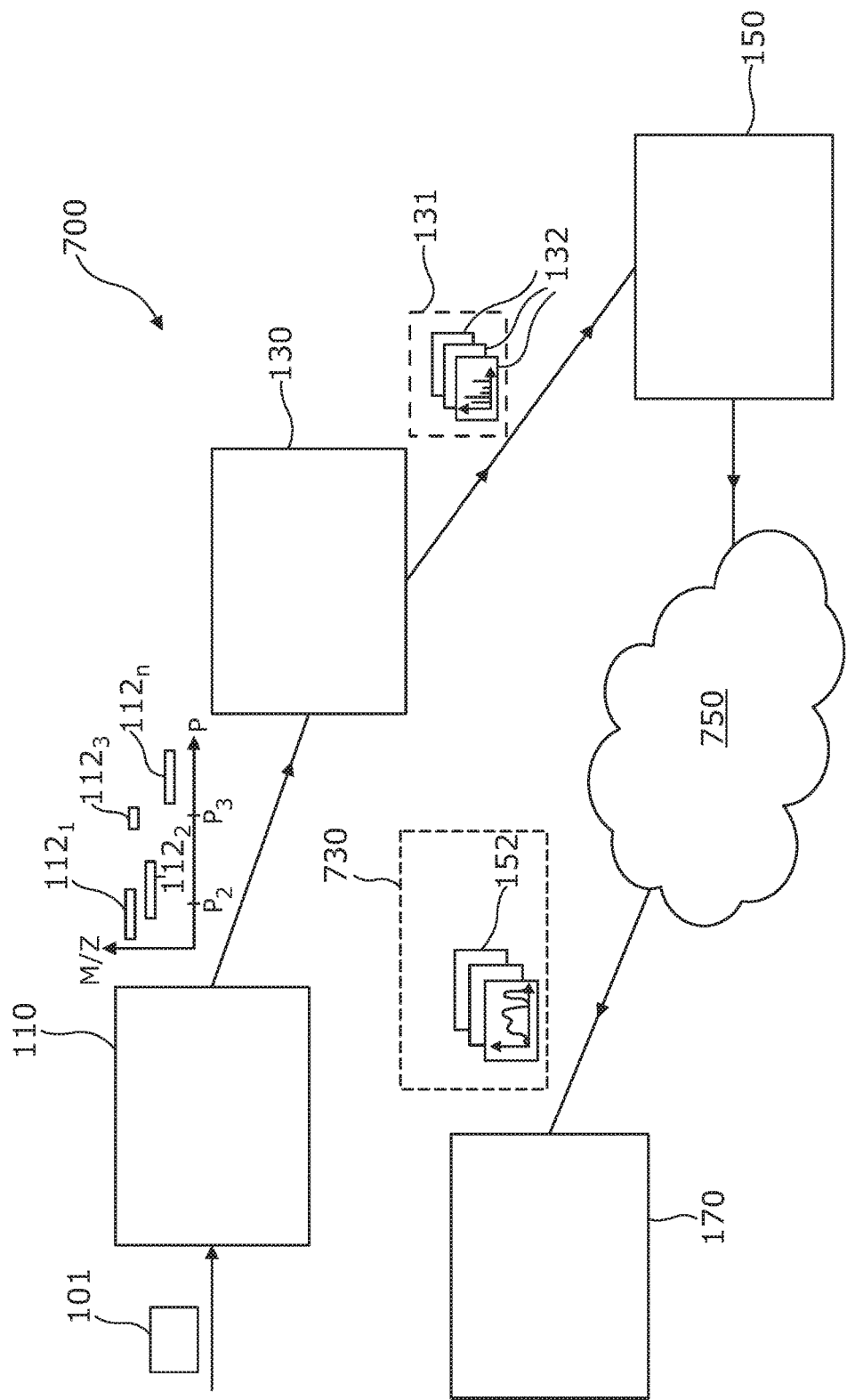
FIG. 7 schematically illustrates a variant example system for coupled separation mass/spectrometry analysis of a sample.

FIG. 7 schematically illustrates a variant example system 700 for separation mass spectrometry analysis of a sample 101. The variant system 700 is a variant of example system 100 discussed previously. The above discussions related to the system 100 of FIG. 7 except in the following respects.

The analysis system 150 is arranged to decompose the mass spectrometry data 131 into a plurality of mass traces 152. It will be appreciated that such decomposition typically comprises repeated extraction of mass traces 152 from the mass spectrometry data 131, such as by any of the methods described previously. Such repeated extraction is usually performed until no further mass traces 152 are extracted. Other criteria for terminating the repeated extraction (or decomposition) may be used, such as any of: a pre-defined number of mass traces 152 are extracted; each centroid (or intensity peak) of the mass spectra 132 of the mass spectrometry data 131 has been included in (or considered for) a mass trace.

The analysis system is arranged to identify erroneous mass traces 152 in the plurality of mass traces 152. Erroneous mass traces 152 may be mass traces 152 with missing centroids, giving rise to spurious mass trace intensity peaks, such as that discussed previously with reference to FIG. 1c. Additionally, or alternatively an erroneous mass trace 152 may be a mass trace 152 comprising less than a pre-defined minimum number of centroids. The pre-defined number of centroids may be set based on curve fitting criteria. For example, the pre-defined number of centroids may be the minimum number of points required to fit a pre-defined curve type to the mass trace 152. Typically, a mass trace 152 with fewer than three centroids is an erroneous mass trace, since it will be appreciated that in the simplest case of a parabola fit at least three data points are needed. Additionally, or alternatively the analysis system may be arranged to apply an event detection algorithm to the mass traces to determine one or more events for each mass trace, as part of identifying the erroneous mass traces 152. The application of event detection methods is discussed previously above, and is well known in the art. Typically, such event detection methods comprise fitting a model peak (or a set of model peaks) to each mass trace. Standard computational fitting techniques, such as least-squares fit are often used to do this. As set out above, mass traces where the fitted model peak satisfies some pre-defined criteria, such as having a maximum, a minimum abundance and/or conformance to the model peak are considered events.

A mass trace may be considered to be erroneous if no such event was detected and/or if the event itself is considered erroneous. Typically an erroneous event is one where the goodness of fit of the model peak to the mass trace is below a pre-defined threshold. There are many ways of measuring the fit of a model peak to data that would be known to the person skilled in the art hence it is not described further herein.

Typically, the goodness-of-fit threshold is chosen based on statistical measures of the mass spectrometry data 131 and/or information regarding the mass spectrometer 130. For example, an expected variability for each point in a mass trace may be a sum of; the ion statistical variation (usually Poisson statistics); the detector noise or noise associated with the mass spectrometer's own detector (e.g. Rayleigh distributed noise for magnitude mode FT/MS data); and variation due to other sources, such as the stability of an ion source or imperfections in automatic gain control.

Given this, the sum of the ion statistical variation (usually Poisson statistics); the detector noise times a reasonable margin (such as a factor of 1-2) may be used as an acceptance criterion for the variance of the intensities of the mass trace with respect to the fitted model peak.

The analysis system is arranged to form a compressed version 730 of the mass spectrometry data 131 from the mass traces 152 and the mass spectrometry data 131 corresponding to the identified erroneous mass traces 152. The compressed version 730 of the mass spectrometry data 131 comprises detected events of the non-erroneous (or good) mass traces and optional mass spectrometry data 131 corresponding to the identified erroneous mass traces 152. An event may comprise any of: a mass centre for a mass trace 152; a separation parameter centre for a mass trace, signal-to-noise ratios (or measures) for a mass trace 152, a measure of the background noise in intensity for a mass trace 152, one or more peak widths for a mass trace. For example, the event for a mass trace 152 may comprise the mass centre of the mass trace; the separation parameter centre of the mass trace intensity peak; and the peak width of the mass trace intensity peak. Typically, the mass spectrometry data 131 corresponding to the identified erroneous mass traces 152 is the centroids of the erroneous mass traces.

In other words, it will be appreciated that the mass spectrometry data 131 is compressed by replacing the mass spectrometry data 131 that relates to non-erroneous mass traces with the corresponding event data for those mass traces, and preserving the mass spectrometry data 131 for the erroneous traces.

For example, a chromatographic peak in mass trace that is comprised of eight intensity peaks in retention time may initially require 24 double precision values to store (made up of m/z value, retention time, and intensity for each intensity peak). With the above compression, if the mass trace is a non-erroneous mass trace then 3 double precision and one single precision value (mass, retention time, intensity, and peak width respectively) may be sufficient. This would be a reduction by a factor of more than 6. As, typically, the majority of mass traces are non-erroneous this provides significant overall compression. Indeed, even in the case where a third of all mass traces are erroneous the mass spectrometry data storage will be reduced by more than a factor of two.

As described above, mass traces with fewer than a pre-defined number of centroids may be classified as erroneous mass traces. However, it will be appreciated that in some cases mass traces with fewer than a predefined number of centroids may be discarded as part of the mass trace generation and/or mass trace providing steps described previously. In these cases such mass traces will not be identified as erroneous mass traces as they will have already been discarded.

For example, the mass trace analysis system 150 may be arranged to discard all mass traces 152 with less than two (or three or another pre-defined number) of data points. In a further example the mass trace analysis system 150 may be arranged to discard all mass traces 152 with less than a predefined number of elements (a short mass trace), unless a peak group determination system (such as that outlined in the International Patent publication WO/2016/145331 or the that in U.S. Pat. No. 7,962,301, both of which are incorporated herein by reference in their entirety) has recognized the signal as part of a peak group. Additionally, or alternatively the mass trace analysis system 150 may be arranged not to discard a short mass trace 152 if the peak is above a pre-defined signal-to-noise threshold, as determined by the peak group determination system. The pre-defined number may preferably be between 1 and a fraction of the peak width in the separation dimension, typically requiring at most half of the peak width. The pre-defined S/N threshold may be relatively high, for example between 10 and 100 (with 10, 20, 50 and 100 being common values). Conversely mass trace analysis system 150 may be arranged to always retain mass traces (for further determination as to whether they are erroneous mass traces or not) of certain pre-defined relative or absolute masses, such as masses from quantitation kits such as NeuCode, iTRAQ or TMT or mass groups for SILAC quantitation. All of these kits would be well known to the person skilled in the art.

The analysis system 150 is connected to the further processing system 170 via a network 750. The network 750 may be any kind of data communication network suitable for communicating or transferring data between the analysis system 150 and the further processing system 170. Thus, the network 170 may comprise one or more of: a wide area network, a metropolitan area network, the Internet, a wireless communication network, a wired or cable communication network, a satellite communications network, a telephone network, etc. The analysis system 150 and the further processing system 170 may be arranged to communicate with each other via the network 750 via any suitable data communication protocol. For example, when the network 750 comprises the Internet, the data communication protocol may be TCP/IP, UDP, SCTP, etc.

The analysis system 150 is arranged to provide the compressed version 730 of the mass spectrometry data 131 to the further processing system 170.

By detecting erroneous mass traces at the mass trace generation stage, the compressed version 730 of the mass spectrometry data 131 is able to retain mass spectrometry data 131 regarding the erroneous mass traces 152. This enables the analysis system 150 to discard the mass spectrometry data 131 regarding the other mass traces, as these mass traces are adequately described for the purposes of the further processing techniques by the event data. The mass spectrometry data 131 regarding the erroneous mass traces 152 are retained so that should further analysis of these erroneous traces be required as part of the further processing techniques, the relevant mass spectrometry data 131 are still available.

In this way, the mass spectrometry data 131 are effectively compressed, given that the event data for a given mass trace is typically significantly smaller than the raw mass spectrometry data 131 corresponding to the mass trace 152. As such the raw mass spectrometry data 131 may be discarded and the compressed version 730 of the mass spectrometry data 131 used in preference. Indeed, it will be appreciated that the analysis module 150 may be located locally to the mass spectrometer 130, reducing the need for large data transfers of the mass spectrometry data 131.

It will also be appreciated that the analysis system 150 may generate the compressed version 730 of the mass spectrometry data 131 in real time with respect to the operation of the mass spectrometer 130. This is because the acquisitions of the mass spectrometer 130 are typically in order of elution parameter, as is the processing of the mass spectrometry data 131 set out above. This real-time operation has the further advantage that the whole set of mass spectrometry data 131 need not be stored at any one time. The mass traces 152 can be checked to see if they are erroneous as they are generated and the relevant mass spectrometry data 131 discarded on the fly.

The compression described above can be used alongside existing techniques for reducing noise in the spectral (or m/z) domain. Examples of these techniques can be found in U.S. Pat. Nos. 7,962,301 and 7,987,060 both of which are incorporated by reference in their entirety. In particular background spectral noise may be compressed using these methods before or after the compression techniques described above are applied. The use of such techniques in the situation described above where mass traces 152 shorter than a pre-defined number of centroids are discarded (rather than being identified as erroneous mass traces) may provide additional compression benefits as the mass spectrometry data corresponding to these short (discarded) mass traces may be compressed, for example as background noise.

It will be appreciated that further processing of the erroneous mass traces may be performed by the compression system. For example, for erroneous mass traces having any of:

multiple convoluted chromatographic peaks;
m/z deflections due to adjacent mass traces;
peaks with a well defined background noise;
pure background or lock masses;
peaks with systematic mass trends or peak tailing;
peaks with a low signal to noise ratio, may be further analysed to produce additional information, allowing the mass spectrum data relating to these mass traces to be discarded in the compressed version of the mass spectrum data in favour of the corresponding event and the additional information. For example, where there are multiple convoluted chromatographic peaks additional mass and time information may be calculated. Where there are m/z deflections due to adjacent mass traces a set of flags (e.g. deflection detected, reference to the interfering peak; mass corrected etc.) may be determined. Where there are peaks with a well-defined background noise and/or pure background or lock masses, the background mass and intensity may be determined and optionally further flags (e.g. lock mass index, reference to neighbouring time slots with the same mass, etc.). Where there are peaks with a low signal to noise ratio the signal to noise ratio may be recorded.

In the above description, mass spectra have been discussed in terms of m/z ratio and intensity. It will be appreciated however that mass spectra can be represented in a number of different ways, for example in terms of mass and relative abundance, mass and intensity, m/z ratio and relative abundance etc. The above discussions apply equally to any other way of representing mass spectra known in the art. Thus the skilled person would appreciate that discussions referring to the term m/z herein may be applied equally to the term mass and vice versa.

It will be appreciated that a separation device 110 as described above may comprise several different separation devices 110 chained together. For example the mass stream produced by a MALDI device may be then introduced to a chromatograph for further separation, with the resulting mass stream being provided to the mass spectrometer 130.

As set out above, event detection frequently makes use of model peaks. While this is described above based on an analytical model, such as a particular peak form (e.g. a Gaussian distribution), it will be appreciated that this model peak may as well be represented as a series of samples. This may especially be convenient, when a mass trace does not conform to a certain simple model but are "self-similar" except for scaling (and of cause shift). This may be especially convenient when model peak information is collected from the mass spectrometry data. The average peak shape may then be compared to a set of known models, from which one is chosen and parameterized if appropriate. When a systematic shape is found that doesn't conform to any of the models in the set, the observed average peak may be represented as a set of samples. The fitting methods and determination of quality factors (e.g. the variance of the measured points vs. the correctly scaled sampled model peak) are not significantly different. Linear or higher order interpolation of a sampled model peak may be necessary to adjust for variations in sample density.

It will be appreciated that the methods described have been shown as individual steps carried out in a specific order. However, the skilled person will appreciate that these steps may be combined or carried out in a different order whilst still achieving the desired result.

It will be appreciated that embodiments of the invention may be implemented using a variety of different information processing systems. In particular, although the figures and the discussion thereof provide an exemplary computing system and methods, these are presented merely to provide a useful reference in discussing various aspects of the invention. Embodiments of the invention may be carried out on any suitable data processing device, such as a personal computer, laptop, server computer, etc. Of course, the description of the systems and methods has been simplified for purposes of discussion, and they are just one of many different types of system and method that may be used for embodiments of the invention. It will be appreciated that the boundaries between logic blocks are merely illustrative and that alternative embodiments may merge logic blocks or elements, or may impose an alternate decomposition of functionality upon various logic blocks or elements.

It will be appreciated that the above-mentioned functionality may be implemented as one or more corresponding modules as hardware and/or software. For example, the above-mentioned functionality may be implemented as one or more software components for execution by a processor of the system. Alternatively, the above-mentioned functionality may be implemented as hardware, such as on one or more field-programmable-gate-arrays (FPGAs), and/or one or more application-specific-integrated-circuits (ASICs), and/or one or more digital-signal-processors (DSPs), and/or other hardware arrangements. Method steps implemented in flowcharts contained herein, or as described above, may each be implemented by corresponding respective modules; multiple method steps implemented in flowcharts contained herein, or as described above, may be implemented together by a single module.

It will be appreciated that, insofar as embodiments of the invention are implemented by a computer program, then a storage medium and a transmission medium carrying the computer program form aspects of the invention. The computer program may have one or more program instructions, or program code, which, when executed by a computer carries out an embodiment of the invention. The term "program" as used herein, may be a sequence of instructions designed for execution on a computer system, and may include a subroutine, a function, a procedure, a module, an object method, an object implementation, an executable application, an applet, a servlet, source code, object code, a shared library, a dynamic linked library, and/or other sequences of instructions designed for execution on a computer system. The storage medium may be a magnetic disc (such as a hard drive or a floppy disc), an optical disc (such as a CD-ROM, a DVD-ROM or a BluRay disc), or a memory (such as a ROM, a RAM, EEPROM, EPROM, Flash memory or a portable/removable memory device), etc. The transmission medium may be a communications signal, a data broadcast, a communications link between two or more computers, etc.

The invention claimed is:

1. A computer implemented method of extracting a mass trace from mass spectrometry data of a mass stream emitted from a separation device as a function of a separation parameter, wherein the mass spectrometry data are generated by analysis in a mass spectrometer, the method comprising:
   receiving the mass spectrometry data, wherein the mass spectrometry data comprise a plurality of mass spectra each obtained for respective values of the separation parameter;
   identifying, from the plurality of mass spectra, a sequence of three or more intensity peaks that are ordered according to the separation parameter, wherein said identifying the sequence of three or more intensity peaks comprises:
      selecting an initial intensity peak at an initial mass, and for each other intensity peak of the sequence of intensity peaks,
         selecting said intensity peak based on at least the mass of an adjacent intensity peak in the sequence of intensity peaks,
   the method further comprising, providing a mass trace, for a given emitted compound of the mass stream, from the identified sequence of intensity peaks.

2. The method according to claim 1, wherein for each other intensity peak of the sequence of intensity peaks, said intensity peak is selected conditional on said intensity peak being at a respective mass that is within a respective range about a respective expected mass, wherein the respective expected mass is determined based on at least the mass of an adjacent intensity peak in the sequence of intensity peaks.

3. The method according to claim 2 wherein the respective expected mass is determined based on an average of the previously selected intensity peaks of the sequence.

4. The method according to claim 3 wherein the average of the previously selected intensity peaks of the sequence is a weighted average.

5. The method according to claim 3 wherein the average of the previously selected intensity peaks of the sequence is a windowed average.

6. The method according to claim 2 wherein the respective range is determined as a function of the intensity of the adjacent intensity peak.

7. The method according to claim 1 wherein the separation device comprises a chromatograph and the separation parameter comprises retention time.

8. The method according to claim 1 wherein the separation parameter comprises any one or more of: ion mobility; pH; ion size; collision cross section; polarizability.

9. The method according to claim 1 wherein the separation device comprises a mass spectrometry imaging device and the separation parameter represents a surface location of a sample provided to the mass spectrometry imaging device.

10. The method according to claim 1 wherein said providing step further comprises providing a separation parameter centre and a mass centre for the mass trace.

11. The method according to claim 10 wherein said providing step comprises applying an event detection algorithm to the mass trace, thereby generating an event corresponding to the mass trace, the event comprising the separation parameter centre and the mass centre.

12. A computer implemented method for compressing mass spectrometry data, the method comprising:
   decomposing the mass spectrometry data into a plurality of mass traces by repeated application of a method according to any one of the preceding claims;
   identifying erroneous mass traces in the plurality of mass traces by applying an event detection algorithm to each of the plurality of mass traces;
   forming a compressed version of the mass spectrometry data from the mass traces and the mass spectrometry data corresponding to the identified erroneous mass traces.

13. The method according to claim 12 wherein the compressed version of the mass spectrometry data comprises the mass spectrometry data corresponding to the identified erroneous mass traces, and one or more events generated by the applying of the event detection algorithm in place of the mass spectrometry data relating to the one or more events.

14. An apparatus arranged to carry out a method according to claim 1.

15. A computer-readable medium storing instructions which, when executed by a processor, causes the processor to carry out a method according to claim 1.

16. An apparatus arranged to carry out a method according to claim 12.

17. A computer-readable medium storing instructions which, when executed by a processor, causes the processor to carry out a method according to claim 12.

* * * * *